(12) United States Patent
Miyashiro et al.

(10) Patent No.: US 12,414,855 B2
(45) Date of Patent: Sep. 16, 2025

(54) TRICUSPID VALVE REPAIR DEVICES AND ASSOCIATED SYSTEMS AND METHODS

(71) Applicant: Half Moon Medical, Inc., Menlo Park, CA (US)

(72) Inventors: Katherine Miyashiro, Menlo Park, CA (US); Hanson S. Gifford, Woodside, CA (US); James I. Fann, Portola Valley, CA (US); Ben F. Brian, Menlo Park, CA (US); Gaurav Krishnamurthy, Mountain View, CA (US); Jose Gonzalez, Fremont, CA (US); Paul Gunning, San Francisco, CA (US); Matthew McLean, San Francisco, CA (US); Neil Zimmerman, Menlo Park, CA (US); Robert O'Grady, San Francisco, CA (US); Douglas S. Sutton, Pacifica, CA (US); Steven K. Stringer, Vista, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 17/456,153

(22) Filed: Nov. 22, 2021

(65) Prior Publication Data
US 2022/0160499 A1    May 26, 2022

Related U.S. Application Data

(60) Provisional application No. 63/116,729, filed on Nov. 20, 2020.

(51) Int. Cl.
*A61F 2/24* (2006.01)
(52) U.S. Cl.
CPC ...... *A61F 2/246* (2013.01); *A61F 2220/0016* (2013.01); *A61F 2230/0056* (2013.01)

(58) Field of Classification Search
CPC .............. A61F 2/246; A61F 2230/0056; A61F 2/2454; A61F 2/2457; A61F 2/2463;
(Continued)

(56) References Cited

U.S. PATENT DOCUMENTS

| 6,869,444 B2 | 3/2005 | Gabbay |
| 7,160,322 B2 | 1/2007 | Gabbay |

(Continued)

FOREIGN PATENT DOCUMENTS

| CN | 103079498 B | 5/2013 |
| DE | 102013017993 A1 | 6/2015 |

(Continued)

OTHER PUBLICATIONS

ISA, PCT Application No. PCT/US2021/072560, International Search Report and Written Opinion mailed Mar. 10, 2022, 18 pages.

(Continued)

*Primary Examiner* — Seema Mathew
(74) *Attorney, Agent, or Firm* — Wentsler LLC

(57) ABSTRACT

Tricuspid valve repair devices and associated systems and methods are disclosed herein. A tricuspid valve repair device configured in accordance with embodiments of the present technology can include, for example, a coaptation member configured to be positioned between one or more native leaflets of the tricuspid valve to at least partially fill a space between the native leaflets. The tricuspid valve repair device can further include one or more fixation mechanisms for securing the coaptation member in position between the leaflets. The fixation mechanisms can include clip mechanisms, lock mechanisms, stabilization members, anchors, and/or other structures configured to engage cardiac anatomy local to or remote from the tricuspid valve, such as (Continued)

the native leaflets, the tricuspid valve annulus, the right ventricular outflow tract, the superior vena cava, the inferior vena cava, and so on.

27 Claims, 31 Drawing Sheets

(58) Field of Classification Search
CPC .... A61F 2/2418; A61F 2/2412; A61F 2/2442; A61F 2/2445; A61F 2/2409
See application file for complete search history.

(56) References Cited

U.S. PATENT DOCUMENTS

| | | | |
|---|---|---|---|
| 8,545,553 B2 | 10/2013 | Zipory et al. | |
| 8,574,290 B2 | 11/2013 | Alameddine | |
| 8,821,570 B2 | 9/2014 | DuMontelle et al. | |
| 8,845,722 B2 | 9/2014 | Gabbay | |
| 9,011,523 B2 | 4/2015 | Sequin | |
| 9,592,118 B2 | 3/2017 | Khairkhahan et al. | |
| 9,592,121 B1 | 3/2017 | Khairkhahan | |
| 9,610,163 B2 | 4/2017 | Khairkhahan et al. | |
| 9,907,652 B2 | 3/2018 | Chau et al. | |
| 10,123,874 B2 | 11/2018 | Khairkhahan et al. | |
| 10,166,098 B2 | 1/2019 | Khairkhahan et al. | |
| 10,226,341 B2 | 3/2019 | Gross et al. | |
| 10,390,714 B2 | 8/2019 | Wolinsky et al. | |
| 10,408,690 B2 | 9/2019 | Gouko et al. | |
| 10,449,046 B2 | 10/2019 | Rafiee | |
| 10,470,883 B2 | 11/2019 | Khairkhahan et al. | |
| 10,478,303 B2 | 11/2019 | Khairkhahan | |
| 10,500,048 B2 | 12/2019 | Khairkhahan et al. | |
| 10,512,542 B2 | 12/2019 | Khairkhahan et al. | |
| 10,531,956 B2 | 1/2020 | Skarsgard | |
| 10,702,386 B2 | 7/2020 | Khairkhahan et al. | |
| 11,000,372 B2 | 5/2021 | Khairkhahan et al. | |
| 11,083,572 B2 | 8/2021 | McLean et al. | |
| 11,173,032 B2 | 11/2021 | Zeng | |
| 11,344,410 B2 | 5/2022 | Hacohen et al. | |
| 11,504,237 B2 | 11/2022 | Gifford, III et al. | |
| 11,633,281 B2 | 4/2023 | Kappetein et al. | |
| 12,053,373 B2 | 8/2024 | Mclean et al. | |
| 12,274,621 B2* | 4/2025 | Dixon | A61F 2/246 |
| 2003/0139677 A1 | 7/2003 | Fonseca et al. | |
| 2003/0199975 A1 | 10/2003 | Gabbay | |
| 2004/0093060 A1 | 5/2004 | Sequin et al. | |
| 2004/0127982 A1 | 7/2004 | Machold et al. | |
| 2005/0010287 A1 | 1/2005 | Macoviak et al. | |
| 2005/0142162 A1 | 6/2005 | Hunter et al. | |
| 2006/0058871 A1* | 3/2006 | Zakay | A61F 2/246 623/2.18 |
| 2007/0038297 A1 | 2/2007 | Bobo, Jr. et al. | |
| 2008/0077235 A1 | 3/2008 | Kirson | |
| 2010/0217382 A1 | 8/2010 | Chau et al. | |
| 2010/0262233 A1 | 10/2010 | He | |
| 2010/0280604 A1 | 11/2010 | Zipory et al. | |
| 2010/0298929 A1 | 11/2010 | Thornton et al. | |
| 2011/0029072 A1 | 2/2011 | Gabbay | |
| 2011/0276130 A1 | 11/2011 | Alameddine | |
| 2012/0197388 A1 | 8/2012 | Khairkhahan et al. | |
| 2012/0197392 A1 | 8/2012 | DuMontelle et al. | |
| 2013/0006352 A1 | 1/2013 | Yaron | |
| 2014/0067048 A1* | 3/2014 | Chau | A61F 2/2412 623/2.1 |
| 2014/0067054 A1* | 3/2014 | Chau | A61F 2/2454 623/2.36 |
| 2014/0343670 A1 | 11/2014 | Bakis et al. | |
| 2014/0358223 A1 | 12/2014 | Rafiee et al. | |
| 2015/0119981 A1* | 4/2015 | Khairkhahan | A61F 2/2466 623/2.36 |
| 2015/0142104 A1 | 5/2015 | Braido | |
| 2015/0148893 A1 | 5/2015 | Braido et al. | |
| 2015/0230919 A1 | 8/2015 | Chau et al. | |
| 2015/0327996 A1 | 11/2015 | Fahim et al. | |
| 2015/0366666 A1 | 12/2015 | Khairkhahan et al. | |
| 2016/0030176 A1* | 2/2016 | Mohl | A61F 2/2454 623/2.11 |
| 2016/0045165 A1 | 2/2016 | Braido et al. | |
| 2016/0045316 A1 | 2/2016 | Braido et al. | |
| 2016/0074164 A1 | 3/2016 | Naor | |
| 2016/0166382 A1 | 6/2016 | Nguyen | |
| 2016/0287387 A1* | 10/2016 | Wei | A61F 2/2454 |
| 2016/0317290 A1* | 11/2016 | Chau | A61F 2/2436 |
| 2016/0324639 A1* | 11/2016 | Nguyen | A61F 2/2409 |
| 2016/0331523 A1* | 11/2016 | Chau | A61F 2/2454 |
| 2017/0056176 A1 | 3/2017 | Rowe et al. | |
| 2017/0065418 A1 | 3/2017 | Skarsgard | |
| 2017/0095332 A1 | 4/2017 | Bruchman | |
| 2017/0112618 A1* | 4/2017 | Li | A61F 2/2445 |
| 2017/0165067 A1 | 6/2017 | Barajas-Torres et al. | |
| 2017/0231759 A1 | 8/2017 | Geist et al. | |
| 2017/0258589 A1* | 9/2017 | Pham | A61F 2/246 |
| 2017/0296706 A1 | 10/2017 | Simon et al. | |
| 2017/0319333 A1 | 11/2017 | Tegels et al. | |
| 2018/0143087 A1 | 5/2018 | Gouko et al. | |
| 2018/0147054 A1 | 5/2018 | Chau et al. | |
| 2018/0243087 A1 | 8/2018 | Kapadia | |
| 2018/0271651 A1 | 9/2018 | Christianson et al. | |
| 2018/0325663 A1* | 11/2018 | Taylor | A61F 2/2412 |
| 2018/0325666 A1 | 11/2018 | Ma | |
| 2019/0000613 A1* | 1/2019 | Delgado | A61B 17/00 |
| 2019/0076247 A1 | 3/2019 | Zeng | |
| 2019/0091047 A1 | 3/2019 | Walsh | |
| 2019/0142590 A1* | 5/2019 | Yeo | A61F 2/2466 623/2.11 |
| 2019/0201191 A1 | 7/2019 | McLean et al. | |
| 2019/0209324 A1 | 7/2019 | Metchik | |
| 2019/0282364 A1 | 9/2019 | Khairkhahan et al. | |
| 2020/0138569 A1* | 5/2020 | Basude | A61F 2/246 |
| 2020/0188108 A1 | 6/2020 | Grimm et al. | |
| 2020/0205978 A1 | 7/2020 | Padala et al. | |
| 2020/0222185 A1 | 7/2020 | Kappetein et al. | |
| 2020/0268512 A1 | 8/2020 | Mohl | |
| 2020/0289265 A1 | 9/2020 | Gifford, III et al. | |
| 2020/0360138 A1 | 11/2020 | Ma | |
| 2020/0397567 A1 | 12/2020 | Khairkhahan | |
| 2021/0022850 A1* | 1/2021 | Basude | A61F 2/2463 |
| 2021/0085462 A1* | 3/2021 | Gifford, III | A61F 2/2463 |
| 2021/0275305 A1 | 9/2021 | Pham et al. | |
| 2021/0307901 A1 | 10/2021 | Rannani | |
| 2021/0330456 A1 | 10/2021 | Hacohen et al. | |
| 2021/0330461 A1* | 10/2021 | Bapat | A61F 2/2457 |
| 2021/0353418 A1 | 11/2021 | Mohl | |
| 2022/0015905 A1* | 1/2022 | Raanani | A61F 2/2445 |
| 2022/0039951 A1 | 2/2022 | Khairkhahan et al. | |
| 2022/0096236 A1* | 3/2022 | Guidotti | A61F 2/2463 |
| 2022/0125579 A1 | 4/2022 | McLean et al. | |
| 2022/0125586 A1 | 4/2022 | Rafiee | |
| 2022/0160499 A1* | 5/2022 | Miyashiro | A61F 2/246 |
| 2022/0160508 A1* | 5/2022 | Miyashiro | A61F 2/2454 |
| 2022/0273433 A1* | 9/2022 | Kuck | A61F 2/2454 |
| 2023/0040083 A1 | 2/2023 | Gifford, III et al. | |
| 2023/0132907 A1* | 5/2023 | McLean | A61F 2/2445 623/2.36 |
| 2023/0270549 A1* | 8/2023 | Guidotti | A61F 2/2457 623/2.11 |
| 2024/0180703 A1* | 6/2024 | Feld | A61F 2/2466 |
| 2024/0207045 A1* | 6/2024 | Orlov | A61F 2/2436 |
| 2024/0245512 A1* | 7/2024 | Padala | A61F 2/2463 |
| 2025/0099241 A1* | 3/2025 | Zimmerman | A61F 2/2466 |

FOREIGN PATENT DOCUMENTS

| | | |
|---|---|---|
| EP | 2819618 A1 | 1/2015 |
| EP | 2918248 A1 | 9/2015 |
| EP | 3167846 A1 | 5/2017 |
| JP | 2001520057 A | 10/2001 |
| JP | 2005504585 A | 2/2005 |
| JP | 2005535384 A | 11/2005 |
| JP | 2007513650 A | 5/2007 |
| JP | 2013528407 A | 7/2013 |
| JP | 2014510563 A | 5/2014 |

(56) References Cited

FOREIGN PATENT DOCUMENTS

| | | | |
|---|---|---|---|
| JP | 2016533798 A | 11/2016 | |
| WO | 2004014258 A1 | 2/2004 | |
| WO | 2005002424 A3 | 1/2005 | |
| WO | 2012177942 A2 | 12/2012 | |
| WO | 2014189974 A1 | 11/2014 | |
| WO | 2014195422 A1 | 12/2014 | |
| WO | 2014207575 A1 | 12/2014 | |
| WO | 2014207575 A2 | 12/2014 | |
| WO | 2015052570 A1 | 4/2015 | |
| WO | 2016178136 A1 | 11/2016 | |
| WO | 2017079279 A1 | 5/2017 | |
| WO | 2017096157 A1 | 6/2017 | |
| WO | 2017156175 A2 | 9/2017 | |
| WO | 2018142186 A1 | 8/2018 | |
| WO | WO2019010370 | 1/2019 | |
| WO | 2019045910 A1 | 3/2019 | |
| WO | 2019143726 A1 | 7/2019 | |
| WO | 2020101676 A1 | 5/2020 | |
| WO | WO2020146548 | 7/2020 | |
| WO | WO2020163112 | 8/2020 | |
| WO | WO2020167677 | 8/2020 | |
| WO | 2021027588 A1 | 2/2021 | |
| WO | 2021113449 A1 | 6/2021 | |
| WO | WO2022109620 | 5/2022 | |
| WO | WO2022109621 | 5/2022 | |

OTHER PUBLICATIONS

ISA, PCT Application No. PCT/US2021/072559, International Search Report and Written Opinion mailed Apr. 14, 2022, 18 pages.
Communication pursuant to Rules 161(1) and 162 EPC for Application No. 21827552.7-1113, mailed Jun. 27, 2023, 3 pages.
ISA, PCT Application No. PCT/US2018/043566, International Search Report and Written Opinion mailed Oct. 24, 2018, 14 pages.
ISA, PCT Application No. PCT/US2020/013953, International Search Report and Written Opinion mailed Apr. 15, 2020, 14 pages.
ISA, PCT Application No. PCT/US2020/022471, International Search Report and Written Opinion mailed Jun. 3, 2020, 17 pages.
ISA, PCT Application No. PCT/US2020/051887, International Search Report and Written Opinion mailed Nov. 27, 2020, 13 pages.
First Office Action, CN Application No. 201880071508.7, mailed Jul. 26, 2022, 8 pages.
Japanese Office Action Application No. 2020-534161, mailed Sep. 5, 2022.
Japanese Final Action Application No. 2020-534161, mailed Jun. 12, 2023, 12 pages with English translation.
Japanese Decision of Grant for Application No. 2020-534161, mailed Feb. 26, 2024, 2 pages.
Indian Office Action Application No. 202017013197, mailed Dec. 9, 2022, 7 pages.
Chinese Notice of Grant, CN Application No. 201880071508.7, mailed Feb. 10, 2023, 2 pages.
Japanese Final Action Application No. 2021-526692, mailed Jul. 20, 2023, 4 pages with English translation.
Japanese Office Action Application No. 2021-526692, mailed Nov. 16, 2022, 7 pages with English translation.
Japanese Decision of Grant for Application No. 2021-526692, mailed Jan. 11, 2024, 1 page.
Indian Office Action Application No. 202117026236, mailed Jan. 20, 2023, 6 pages.
Japanese Office Action Application No. 2021-541298, mailed Dec. 4, 2023, 13 pages with English translation.
Japanese Office Action Application No. 2021-541298, mailed May 28, 2024, 2 pages.
Canadian Office Action for Application No. 3,074,477 mailed Nov. 29, 2024, 7 pages.
Examination Report for New Zealand Application No. 762744 mailed Dec. 2, 2024, 4 pages.
Japanese Office Action Application No. 2023-175147, mailed Feb. 3, 2025, 8 pages with English translation.
Australian Office Action for Application No. 2018324358, mailed Aug. 2, 2023, 4 pages.
Australian Notice of Acceptance for Application No. 2018324358, mailed Mar. 4, 2024, 3 pages.
ISA, PCT Application No. PCT/US2022/048999, International Search Report and Written Opinion mailed Mar. 15, 2023, 23 pages.
PCT Search Report and Written Opinion, Appl. No. PCT/US2018/061126, dated Jul. 9, 2019, 12 pages.
European Search Report, Application No. 24212836.1, mailed Feb. 18, 2025, 3 pages.
Australian Office Action for Application No. 2024204015, mailed Feb. 27, 2025, 2 pages.
Chinese First Office Action, Application No. 201880100627.0, mailed Feb. 2, 2024, 6 pages.
Chinese Notice of Grant, CN Application No. 201880100627.0, mailed Jun. 12, 2024, 2 pages.
Japanese Office Action Application No. 2022-517424, mailed Apr. 15, 2024, 12 pages, with English translation.
Japanese Decision of Grant Application No. 2022-517424, mailed Feb. 10, 2025, 1 page.
Japanese Office Action Application No. 2021-553330, mailed Apr. 22, 2024, 4 pages, with English translation.
Australian Office Action for Application No. 2018449153, mailed Jul. 26, 2024, 3 pages.

* cited by examiner

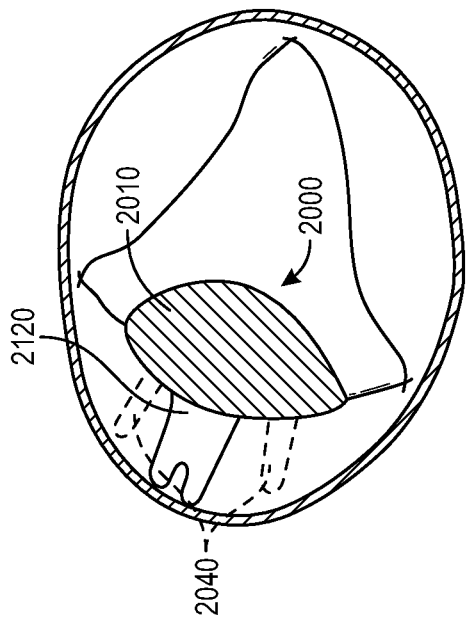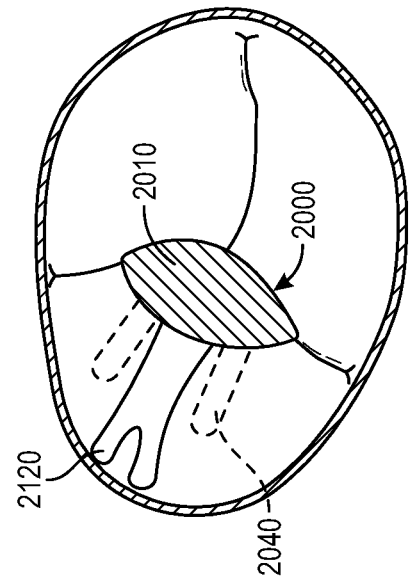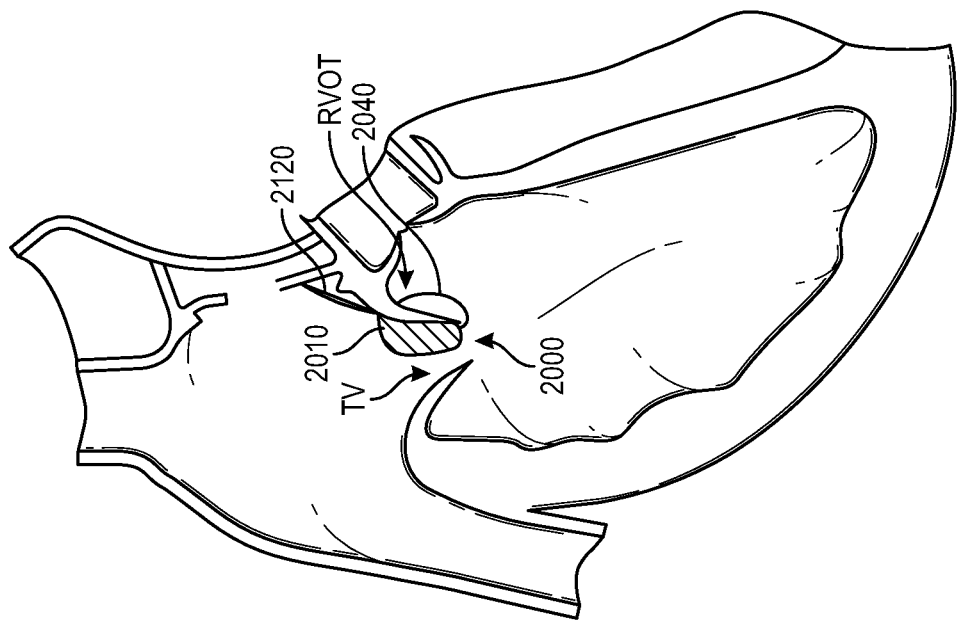

TRICUSPID VALVE REPAIR DEVICES AND ASSOCIATED SYSTEMS AND METHODS

CROSS-REFERENCE TO RELATED APPLICATION

This application claims the benefit of U.S. Provisional Patent Application No. 63/116,729, titled "TRICUSPID VALVE REPAIR DEVICES AND ASSOCIATED SYSTEMS AND METHODS," and filed Nov. 20, 2020, which is incorporated herein by reference in its entirety.

TECHNICAL FIELD

The present technology is directed to devices, systems, and methods for repairing a tricuspid valve, and more particularly to valve repair devices configured to be implanted at the tricuspid valve.

BACKGROUND

Proper functioning of the tricuspid valve of a human patient can be affected by valve regurgitation, valve prolapse, and/or valve stenosis. Tricuspid valve regurgitation can occur when the native leaflets of the tricuspid valve fail to coapt into apposition at peak contraction pressures such that blood leaks past the valve from the right ventricle past the tricuspid valve and into the right atrium. Several structural factors may affect the proper closure of the tricuspid valve leaflets. For example, an enlarged tricuspid valve annulus caused by dilation of heart muscle may prevent proper coaptation of the leaflets during systole. Other conditions involve a stretch or tear in the chordae tendineae—the tendons connecting the papillary muscles to the tricuspid valve leaflets—which may also affect proper closure of the valve leaflets. A ruptured chordae tendineae, for example, may cause a valve leaflet to prolapse (e.g., abnormally bulge up) into the right atrium due to inadequate tension on the leaflet, which can also lead to valve regurgitation. Abnormal backflow can also occur when the papillary muscles are compromised (e.g., due to ischemia) such that the affected papillary muscles do not contract sufficiently to effect proper closure during systole. Normal tricuspid valve functioning can also be affected by valve stenosis (e.g., a narrowing of the valve orifice) which, for example, can impede filling of the right ventricle during diastole.

Tricuspid valve regurgitation is often treated using diuretics and/or vasodilators to reduce the amount of blood flowing back into the right atrium. Other treatment methods, such as surgical approaches (open and intravascular), have also been used to either repair or replace native tricuspid valves. For example, cinching or resecting portions of the dilated annulus are typical repair approaches. Cinching of the annulus has been accomplished by implanting annular or peri-annular rings which are generally secured to the annulus or surrounding tissue. Other repair procedures have also involved suturing or clipping of the valve leaflets into partial apposition with one another. Alternatively, more invasive procedures replace the entire valve with mechanical valves or biological tissue. These invasive procedures are conventionally done through large open thoracotomies and are thus very painful, have significant morbidity, and require long recovery periods.

However, with many repair and replacement procedures, the durability of the devices or improper sizing of annuloplasty rings or replacement valves may cause complications. Moreover, many of the repair procedures depend upon the skill of the cardiac surgeon since poorly or inaccurately placed sutures may affect the success of procedures.

BRIEF DESCRIPTION OF THE DRAWINGS

Many aspects of the present disclosure can be better understood with reference to the following drawings. The components in the drawings are not necessarily to scale. Instead, emphasis is placed on clearly illustrating the principles of the present disclosure.

FIG. 21A is a side cross-sectional view of the valve repair device of FIGS. 20A-20C including an atrial stabilization member and implanted at the tricuspid valve in accordance with embodiments of the present technology. FIGS. 21B and 21C are transverse cross-sectional views of the valve repair device of FIG. 21A during diastole and systole, respectively, in accordance with embodiments of the present technology.

DETAILED DESCRIPTION

Figure 1:
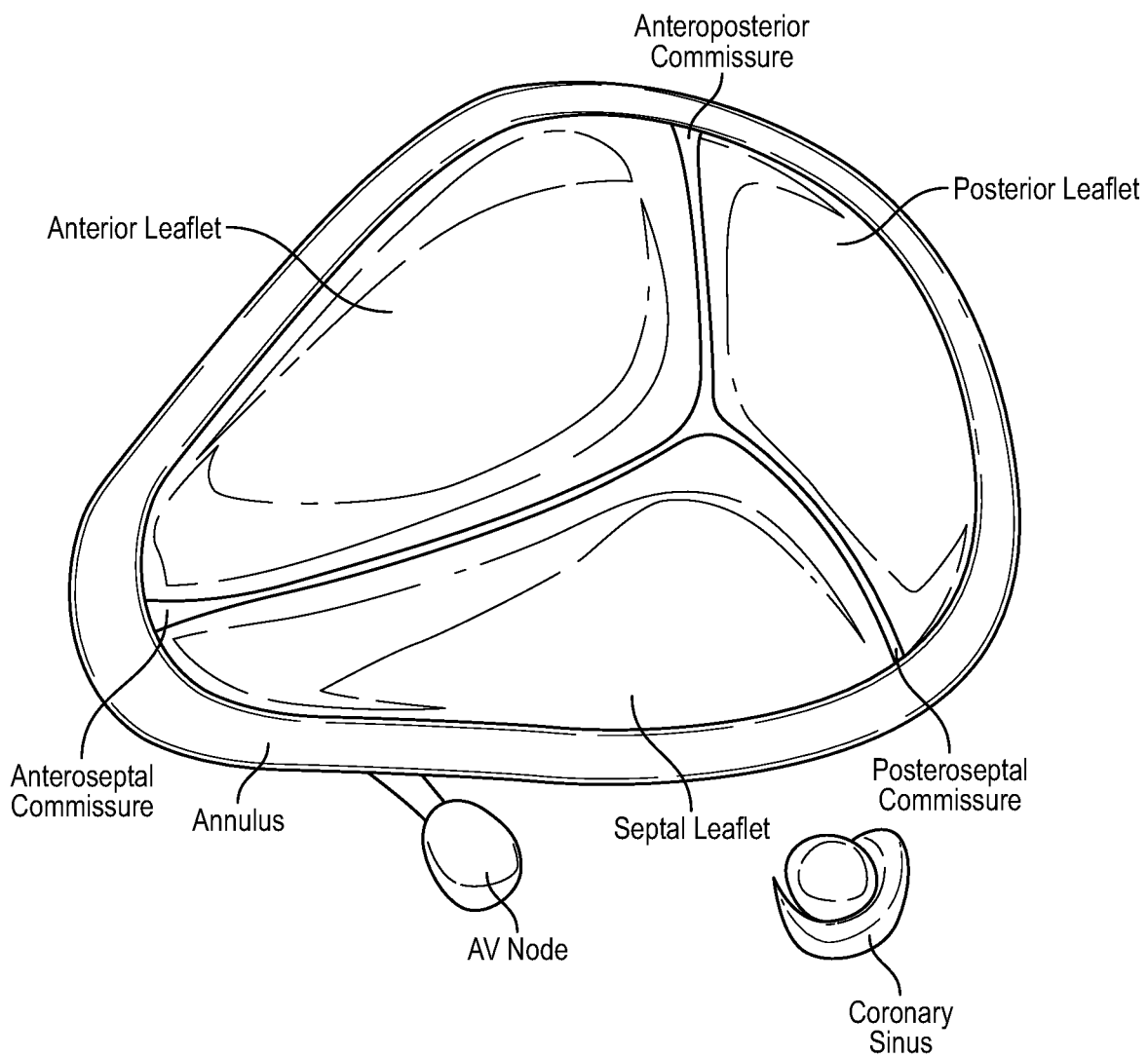
FIG. 1 is a diagram of a tricuspid valve and surrounding anatomy at which a tricuspid valve repair device can be implanted in accordance with embodiments of the present technology.

The present technology is directed to tricuspid valve repair devices and associated systems and methods. In some embodiments, for example, a tricuspid valve repair device (also referred to herein as a "valve repair device," "coaptation assist device," "implant device," and iterations thereof) includes features that anchor to native anatomy of a heart of a patient, such as one or more of the native leaflets of the tricuspid valve of a human patient. For example, the tricuspid valve repair device can include (i) a coaptation member (also referred to as a "coaptation structure," "space filler," "filler," "baffle," "intravalvular body," "intermediate structure," and iterations thereof) positioned at least partially between the native tricuspid valve leaflets, and (ii) one or more clip mechanisms that secure the coaptation member in position relative to the native leaflets. The coaptation member can at least partially fill a regurgitant orifice in the tricuspid valve and provide a new coaptation surface for the native leaflets to seal around. The coaptation member can also push a portion of the native leaflets outward toward the right ventricular wall, while reducing or minimizing disruption of the remaining portion of the native leaflets. The clip mechanisms can engage the ventricular and/or the atrial side of the native leaflets to secure the position of the coaptation member relative to the tricuspid valve.

In some embodiments, a tricuspid valve repair device in accordance with additional embodiments of the present technology can include (i) a coaptation member positioned between the native tricuspid valve leaflets, and (ii) one or more anchors and/or brace members that secure the coaptation member to anatomy of the right heart other than the native tricuspid valve leaflets. For example, the anchors can be secured to the right atrial wall, right ventricular wall, tricuspid valve annulus, one or more tricuspid leaflets, right ventricular outflow tract, inferior vena cava, superior vena cava, coronary sinus, and/or other portions of the anatomy of the right heart of the patient.

Specific details of several embodiments of the present technology are described herein with reference to FIGS. 1-27C. The present technology, however, can be practiced without some of these specific details. In some instances, well-known structures and techniques often associated with catheter-based delivery systems, prosthetic tricuspid heart valves, and the like, have not been shown in detail so as not to obscure the present technology. The terminology used in the description presented below is intended to be interpreted in its broadest reasonable manner, even though it is being used in conjunction with a detailed description of certain specific embodiments of the disclosure. Certain terms can even be emphasized below; however, any terminology intended to be interpreted in any restricted manner will be overtly and specifically defined as such in this Detailed Description section.

The accompanying Figures depict embodiments of the present technology and are not intended to be limiting of its scope. The sizes of various depicted elements are not necessarily drawn to scale, and these various elements can be arbitrarily enlarged to improve legibility. Component details can be abstracted in the Figures to exclude details such as position of components and certain precise connections between such components when such details are unnecessary for a complete understanding of how to make and use the present technology. Many of the details, dimensions, angles, and other features shown in the Figures are merely illustrative of particular embodiments of the disclosure. Accordingly, other embodiments can have other details, dimensions, angles, and features without departing from the spirit or scope of the present technology.

With regard to the terms "distal" and "proximal" within this description, unless otherwise specified, the terms can reference a relative position of the portions of a catheter subsystem with reference to an operator and/or a location in the vasculature. Also, as used herein, the designations "rearward," "forward," "upward," "downward," etc., are not meant to limit the referenced component to use in a specific orientation. It will be appreciated that such designations refer to the orientation of the referenced component as illustrated in the Figures; the systems of the present technology can be used in any orientation suitable to the user.

The headings provided herein are for convenience only and should not be construed as limiting the subject matter disclosed.

I. OVERVIEW

FIG. 1 is a diagram of a tricuspid valve and surrounding anatomy at which a cardiac valve repair device can be implanted in accordance with embodiments of the present technology. The tricuspid valve is an atrio-ventricular valve separating the right atrium from the right ventricle, and is placed in a more apical position than the mitral valve. The tricuspid valve lies within the right trigone of the fibrous skeleton of the heart. The tricuspid annulus (a fibrous or membranous structure) constitutes the anatomical junction between the right ventricle and the right atrium, and provides a firm support structure for the tricuspid valve. The annulus is less fibrous than other annuli and slightly larger than the mitral valve annulus.

The tricuspid valve has an ovoid shape and includes an anterior leaflet (also referred to as an infundibular or anterosuperior leaflet), a septal leaflet (also referred to as a medial leaflet), and a posterior leaflet (also referred to as an inferior or marginal leaflet). The anterior and septal leaflets are larger than the posterior leaflet. The fixed ends of the leaflets are attached to the annulus. The tricuspid valve has (i) a posteroseptal commissure that defines a distinct area where the septal and posterior leaflets come together at their insertion into the annulus, a (ii) an anteroseptal commissure that defines a distinct area where the septal and anterior leaflets come together at their insertion into the annulus, and (iii) an anteroposterior commissure that defines a distinct area where the anterior and posterior leaflets come together at their insertion into the annulus. The commissures can appear more like indentations than true commissures, and several millimeters of valvular tissue separate the free edges of the commissures from the annulus.

The septal leaflet has more support from the fibrous trigone than the anterior or posterior leaflets. Therefore, tricuspid regurgitation from annular dilation often occurs due to the loss of coaptation between the anterior and posterior leaflets. In addition to annular dilation, leaflet coaptation can also be adversely affected by annular calcification. The tricuspid annulus is surrounded by several important anatomic structures, including the left pulmonary artery, the coronary sinus, and the AV node. As a result, implanted cardiac devices at the tricuspid valve need to be positioned to accommodate the asymmetrical anatomy of the tricuspid valve without impacting the surrounding cardiac structures.

FIGS. 2A-2D are a front view, a side view, a rear view, and a top view, respectively, of a tricuspid valve repair device 200 ("device" or "valve repair device") that can be implanted in a heart of a subject (e.g., a human patient) in accordance with embodiments of the present technology. Referring to FIGS. 2A-2D together, the device includes a coaptation member 210, a stabilization 220 member extending from the coaptation member 210, and a pair of clip mechanisms 230 (also referred to as "capture clips") movably (e.g., hinged, pivotably, rotatably) coupled to the coaptation member 210. In some embodiments, the device 200 can include some features generally similar or identical to one or more of the implantable devices described in (i) U.S. patent application Ser. No. 16/044,447, titled "PROSTHETIC LEAFLET DEVICE," and filed Jul. 24, 2018; (ii) International Patent Application No. PCT/US2018/061126, titled "LEAFLET EXTENSION FOR CARDIAC VALVE LEAFLET," and filed Nov. 14, 2018; (iii) U.S. patent application Ser. No. 16/745,246, titled "IMPLANTABLE COAPTATION ASSIST DEVICES WITH SENSORS AND ASSOCIATED SYSTEMS AND METHODS," and filed Jan. 16, 2020; (iv) U.S. patent application Ser. No. 16/817,464, titled "CARDIAC VALVE REPAIR DEVICES WITH ANNULOPLASTY FEATURES AND ASSOCIATED SYSTEMS AND METHODS," and filed Mar. 12, 2020; and/or (v) U.S. patent application Ser. No. 17/027,681, titled "VALVE REPAIR DEVICES WITH COAPTATION STRUCTURES AND MULTIPLE LEAFLET CAPTURE CLIPS," and filed Sep. 21, 2020; each of which is incorporated herein by reference in its entirety. Any of the valve repair devices disclosed herein can be delivered to the tricuspid valve intravascularly (e.g., trans-septal delivery via the femoral or axial vein), percutaneously (e.g., transapically), and/or surgically.

In the illustrated embodiment, the coaptation member 210 is configured to (i) fill at least a portion of a regurgitant orifice between the native leaflets of the tricuspid valve, (ii) displace at least a portion of one or more of the native leaflets, and/or (iii) provide a prosthetic coaptation surface for one or more of the native leaflets. The clip mechanisms 230 are configured to be positioned on the ventricular (e.g., sub-annular) side of the tricuspid valve and to extend behind and grasp portions of one or more of the native leaflets to affix the leaflets to the coaptation member 210. The stabilization 220 member is configured to be positioned at least partially on the atrial (e.g., supra-annular) side of the tricuspid valve and to contact the atrial sides of one or more of the native leaflets and/or other portions of the cardiac anatomy (e.g., the right atrial wall) to stabilize and secure the position of the coaptation member 210 relative to the tricuspid valve. The stabilization member 220 can also serve to inhibit or even prevent prolapse of the coaptation member 210 during ventricular systole. The stabilization member 220 can also serve to provide a platform for tissue ingrowth and long-term fixation. In the illustrated embodiment, the coaptation member 210 has a trapezoidal side-cross sectional shape and an almond-like transverse cross-sectional shape. The coaptation member 210 can further include a pair of recesses 211 (FIG. 2C) for receiving at least a portion of the clip mechanisms 230.

In the illustrated embodiment, the stabilization member 220 includes a frame 221 having an M-like shape covered by a covering 222. In other embodiments, the frame 221 can have other shapes such as, for example, circular, elliptical, polygonal, irregular, rectilinear, and so on. The frame 221 can be a wireform, braid, or laser-cut stent-like structure formed from a suitably strong biocompatible material such as, for example, stainless steel, nickel-titanium alloys (e.g., nitinol), and/or other suitable stent materials. In some aspects of the present technology, the M-like shape of the frame 221 can provide the stabilization member with lateral stiffness (e.g., from side to side along the stabilization member), while preserving torsional and front-to-back stability so as not to translate loads to/from the coaptation member 210. In some embodiments, the covering 222 (e.g., fabric, graft material) can extend over at least a portion of the frame 221 to at least partially enclose the frame 221 and provide a smooth, atraumatic surface for contacting with the right atrium and/or other portions of the cardiac anatomy while promoting ingrowth into the annulus and right atrium. In some embodiments, the stabilization member 220 can have frictional elements (not shown) which engage the supra-annular and annular tissue and provide additional fixation and stability.

In some embodiments, the coaptation member 210 can extend away from a downstream portion of the stabilization member 220 along a flow axis of the device 200, and at least a portion of the coaptation member 210 can extend radially inward from the stabilization member 220 to, for example, fill a portion of the native valve orifice. In the illustrated embodiment, the stabilization member 220 is angled or biased outwardly from the coaptation member 210 by an angle Ang (FIG. 2B) of between about 10°-75° (e.g., about 15°, about 45°, more than about) 45° to, for example, (i) provide stiffness and support for the coaptation member 210 and/or (ii) push a portion of an adjacent native leaflet back from the tricuspid valve opening and approximate a closed position of the native leaflet when the device 200 is implanted at the tricuspid valve. In some embodiments, the angle Ang can be selected to inhibit the coaptation member 210 from contacting the right ventricular wall during the cardiac cycle and, in particular, during systole. In some embodiments, the coaptation member 210 is more centrally located within the tricuspid valve orifice. The coaptation member 210 can be substantially stationary (e.g., little to no movement) during cardiac cycles such that the position of the coaptation member 210 relative to the stabilization member 220 is at least substantially fixed when the device 200 is deployed at the tricuspid valve. Thus, unlike native leaflets that move back and forth to open and close the native tricuspid valve, the coaptation member 210 can remain stationary during diastole and systole. In some embodiments, the coaptation member 210 does undergo some movement during cardiac cycling.

An outer portion 212 of the coaptation member 210 may have a smooth, atraumatic surface (also referred to as a "coaptation surface") for coapting with at least a portion of one or more opposing native leaflets, whereas an opposing inner portion 213 of the coaptation member 210 adjacent the clip mechanisms 230 can displace and engage at least a portion of another native leaflet. In some embodiments, the inner portion 213 and/or the outer portion 212 may include friction elements that engage the native leaflets. The coaptation member 210 can include an inner expandable frame structure (obscured in FIGS. 2A-2D; e.g., a mesh structure, a laser-cut stent frame) made from a plurality of connected struts that define an at least partially hollow interior space when the device 200 is in the illustrated deployed state. Portions of the frame structure may be disconnected allowing portions of the struts to slide over one another and/or move apart from one another to facilitate a low profile in a delivery state and/or adjustability of the coaptation member 210 dimensions. In some embodiments, the coaptation member 210 or portions thereof can be integral with the stabilization member 220. In other embodiments, the coaptation member 210 is a separate structure that is connected to a portion of the stabilization member 220 during manufacturing using welding, rivets, adhesives, connectors, sutures and fabric, and/or other suitable connection mechanisms.

The coaptation member 210 can include one or more access openings 219, such as slits, valves, and/or holes that provide access to the interior of the coaptation member 210 and components therein during delivery and/or retrieval. For example, the access openings 219 can provide access to delivery system connectors that allow for manipulation of the coaptation member 210 and/or clip actuation mechanisms for opening and closing the clip mechanisms 230. Further, the cavity of the coaptation member 210 may house extension members, supplemental clips, and/or other components that may be optionally deployed during implant procedures.

Figure 2A:
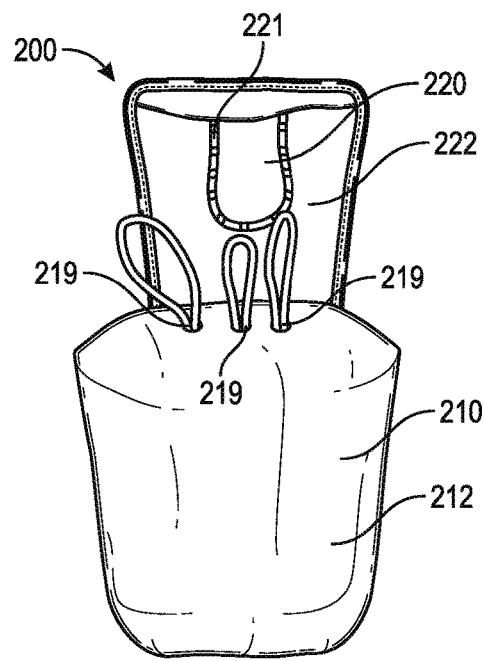
FIGS. 2A-2D are a front view, a side view, a rear view, and a top view, respectively, of a tricuspid valve repair device that can be implanted in a heart of a subject in accordance with embodiments of the present technology.
Figure 2B:
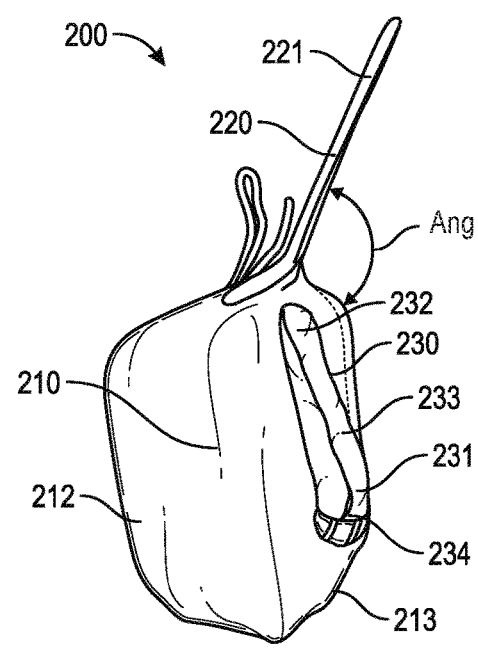
Figure 2C:
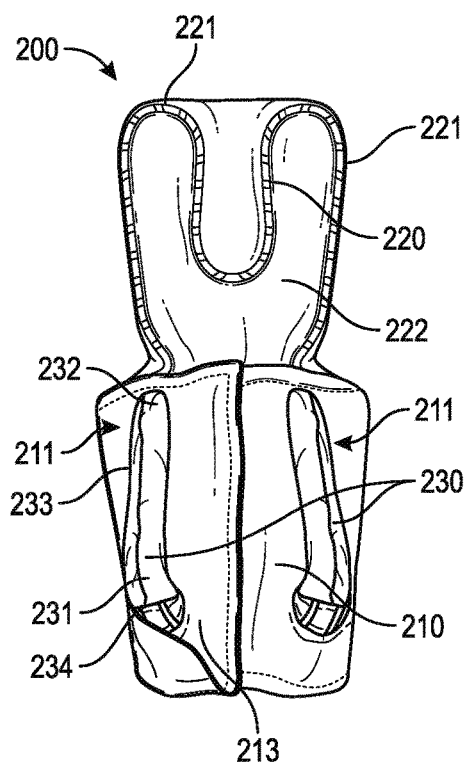
Figure 2D:
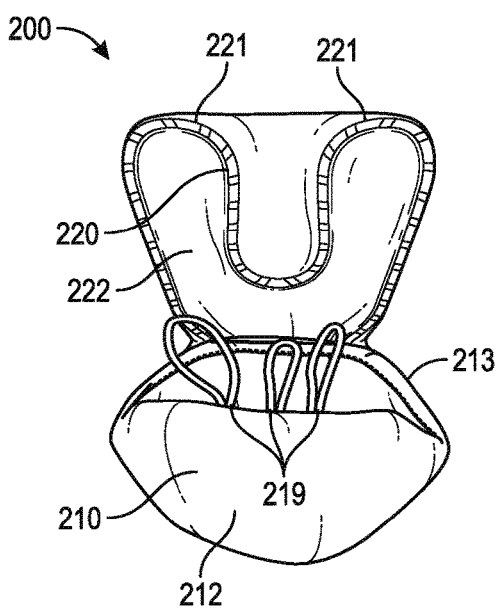
Figure 3A:
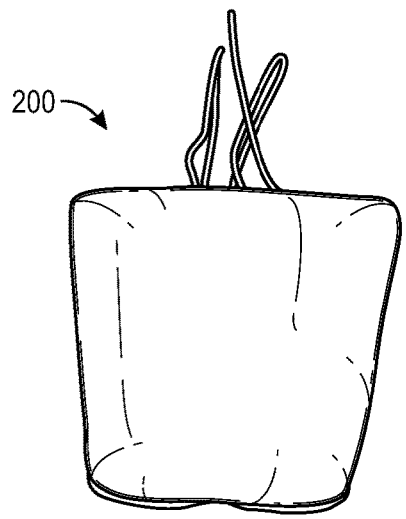
FIGS. 3A-3D are a front view, a side view, a rear view, and a top view, respectively, of the valve repair device of FIGS. 2A-2D with a stabilization member omitted in accordance with embodiments of the present technology.
Figure 3B:
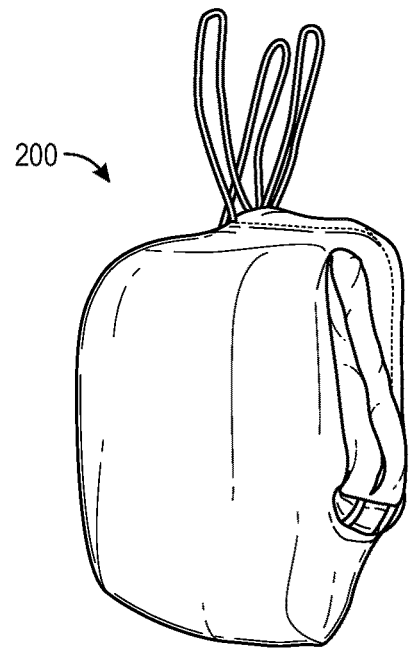
Figure 3C:
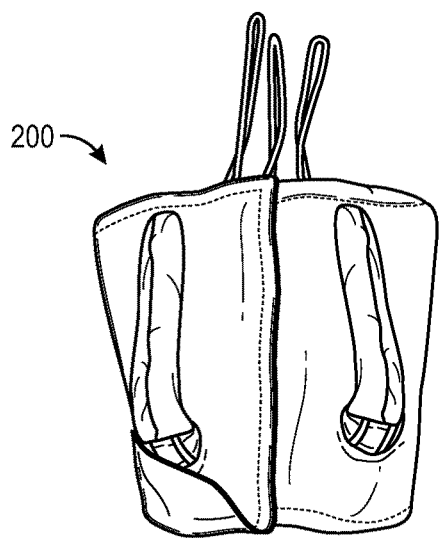
Figure 3D:
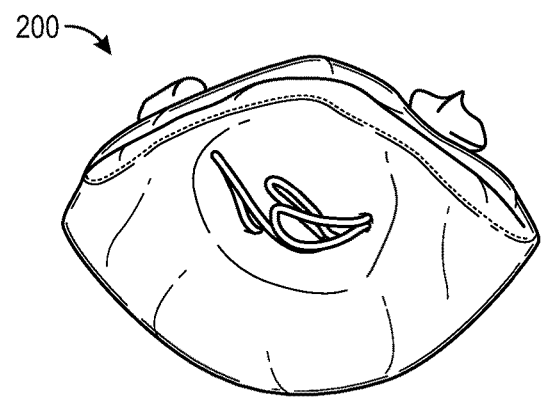
Figure 4A:
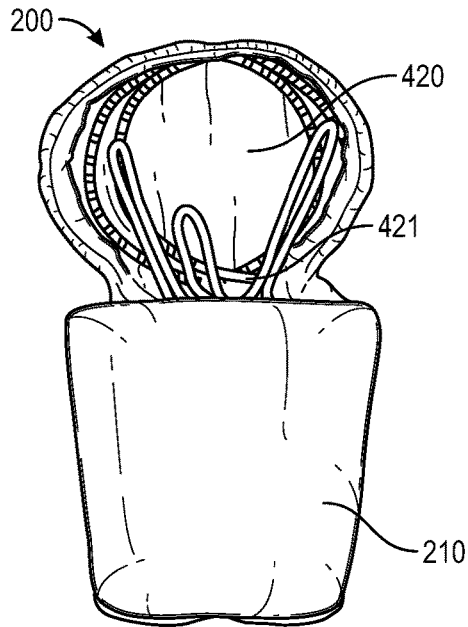
FIGS. 4A-4D are a front view, a side view, a rear view, and a top view, respectively, of the valve repair device of FIGS. 2A-2D including a flexible, generally-round stabilization member in accordance with embodiments of the present technology.
Figure 4B:
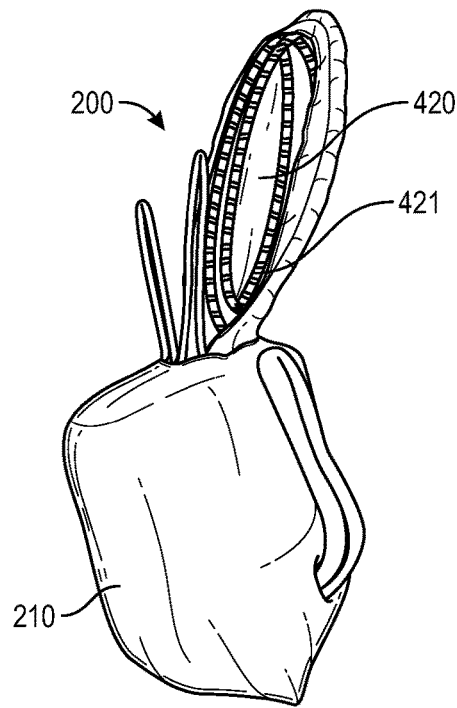
Figure 4C:
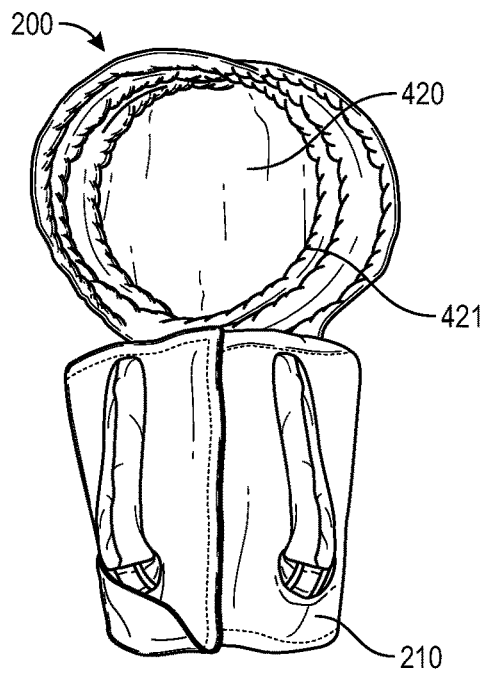
Figure 4D:
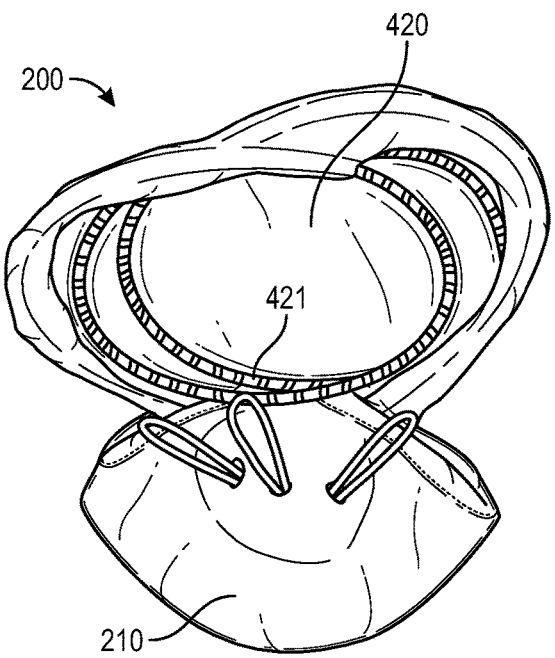

The clip mechanisms 230 extend from the coaptation member 210 (e.g., the inner portion 213 of the coaptation member) to allow the clip mechanisms 230 to extend behind and capture one or more native leaflets positioned on one or multiple sides of the coaptation member 210. With reference to FIGS. 2B and 2C, the clip mechanisms 230 can include a base portion 231 (also referred to as a "first portion") affixed to the coaptation member 210, a free end portion 232 (also referred to as a "second portion") unaffixed to the coaptation member 210, and an articulatable arm member 233 that extends from the base portion 231 and forms the free end portion 232. The base portion 231 can be attached to the coaptation member 210 by welding, riveting, adhesives, sutures, and/or other coupling mechanisms, or may be an extension of the coaptation member frame. The arm member 233 can extend from the base portion 231 in an upstream direction (e.g., toward the stabilization member 220) along a length of the coaptation member 210. For example, the arm member 233 can extend only partway up the coaptation member 210 and along the length of the coaptation member 210 to the downstream end of the stabilization member 220. In some embodiments, the arm member 233 may form an inverted U-like shape and flare outwardly to form a wider section where the arm member 233 clamps against the native leaflet. In other embodiments, the arm member 233 may have other suitable shapes for engaging leaflets and/or may include extensions at the distal-most end that engage sub-annular tissue for additional sub-annular stabilization and fixation.

The arm member 233 can be made from one or more wires, struts, and/or other semi-rigid/rigid structures with sufficient rigidity to clamp against a native leaflet and/or sub-annular tissue. In some embodiments, the arm member 233 includes a fabric covering, a biocompatible foam or other type of padding, and/or a coating on the rigid member to provide (i) a smooth surface at the arm root to reduce trauma to the leaflets and/or surrounding tissue, (ii) additional surface area for leaflet engagement, (iii) a platform for tissue ingrowth, and/or (iv) to provide additional friction to prevent leaflet slip-out. In some embodiments, the arm member 233 and/or other portions of the clip mechanism 230 can include spikes, tines, corrugations, or other frictional features (not shown) that enhance the stability and fixation to the native leaflet.

The clip mechanism 230 can further include an actuation mechanism 234, such as a spring-loaded lever, that acts on the arm member 233 to move it between a closed position (shown in FIGS. 2A-2D; also referred to as a "closed state," "closed configuration," or "first state") and an open position (also referred to as an "open state," "open configuration," or "second state"). In the closed state, the arm member 233 is positioned close to or against the surface of the coaptation member 210 in the corresponding recess 211, with at least a portion of the arm member 233 pressed against the surface of the coaptation member 210 to provide for leaflet engagement. In the open state, the articulatable arm member 233 extends away from the coaptation member 210 (e.g., forming a V-shape or L-shape with the surface of the coaptation member 210) to allow the free end portion 232 to extend behind a native leaflet and receive the native leaflet between the arm member 233 and the surface of the coaptation member 210. In some embodiments, the actuation mechanism 234 holds the clip mechanism 230 in a normally closed state (e.g., due to a spring force) such that (i) the clip mechanism 230 is in the closed state during device delivery and (ii) manipulation of the actuation mechanism 234 moves the clip mechanism 230 to the open state. In other embodiments, the clip mechanism 230 is arranged in a normally open state.

The actuation mechanism 234 can be a spring-loaded lever (e.g., a nitinol wire, laser cut nitinol or Co—Cr sheet) operably coupled to a portion of a delivery system (not shown) that can be manipulated to move the clip mechanism 230 between the open and closed positions. For example, a tendon (made of suture or nitinol wire) can be attached to the spring-loaded lever 234, extend alongside or through the body of the coaptation member 210 and through a delivery catheter to an external handle assembly. A clinician can pull on or otherwise apply tension to the tendon, which translates this force to the lever, thereby moving the arm member 233 between the closed and open positions. In other embodiments, the actuation mechanism 234 may have different actuation means, such as other springs, clamps, pulleys, interfacing threaded members, and/or further actuation mechanisms described in International Patent Application No. PCT/US2018/061126, filed Nov. 14, 2018. Further, because each clip mechanism 230 includes its own actuation mechanism 234, the clip mechanisms 230 can be independently actuated. As described in detail below, in some embodiments the device 200 can include more than two clip mechanisms 230 and/or one of the clip mechanisms 230 may be omitted. The actuation mechanism 234 for the clip mechanism 230 can also have a locking mechanism to prevent clip actuation after deployment.

Figure 5A:
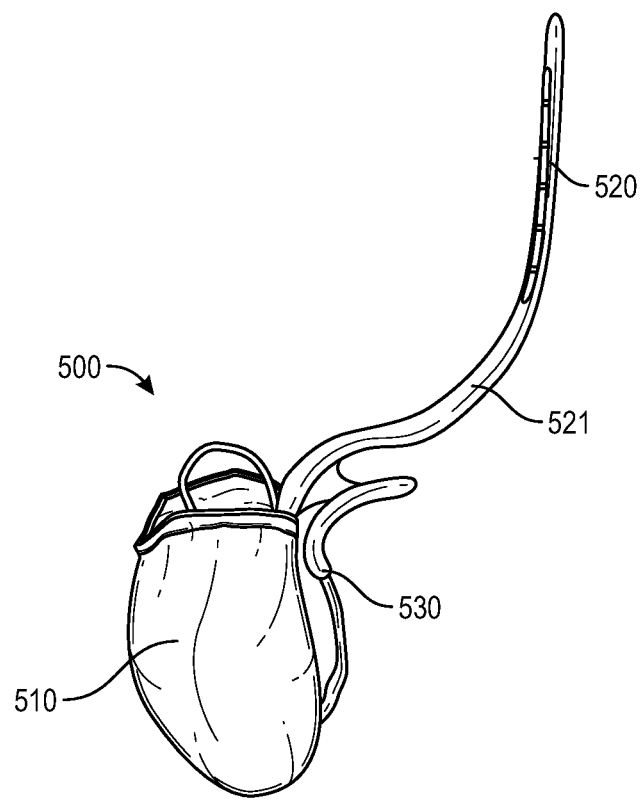
FIGS. 5A and 5B are a side view and a rear view, respectively, of the valve repair device of FIGS. 2A-2D including an elongate-curved stabilization member in accordance with embodiments of the present technology.
Figure 5B:
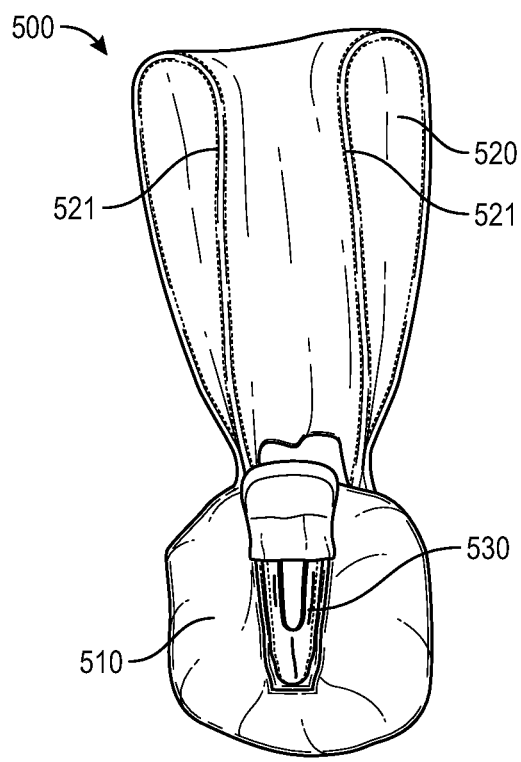
Figure 6A:
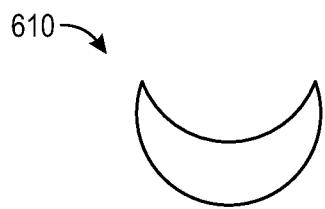
FIGS. 6A-6H are transverse cross-sectional views of various coaptation members in accordance with embodiments of the present technology.
Figure 6B:
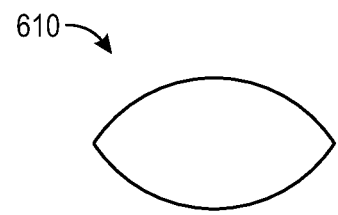
Figure 6C:
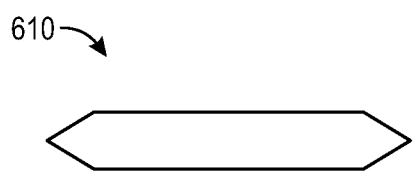
Figure 6D:
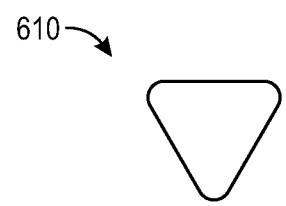
Figure 6E:
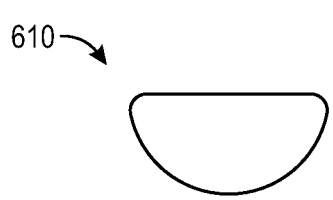
Figure 6F:
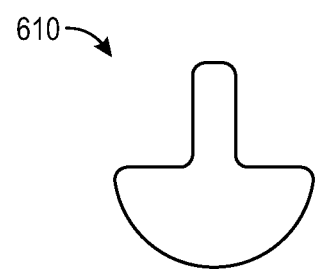
Figure 6G:
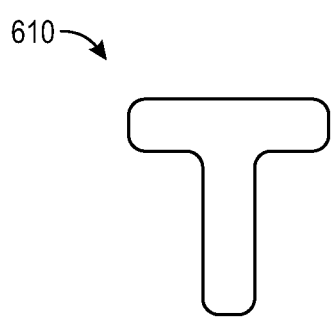
Figure 6H:
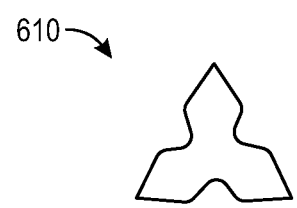
Figure 7A:
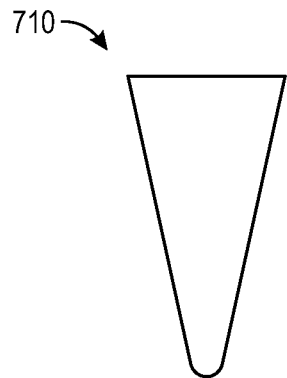
FIGS. 7A-7L are side cross-sectional views of various coaptation members in accordance with embodiments of the present technology.
Figure 7B:
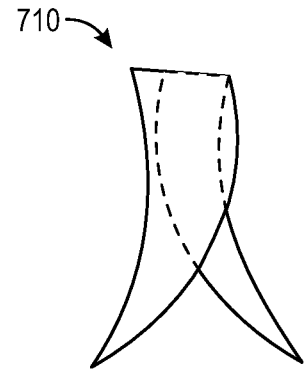
Figure 7C:
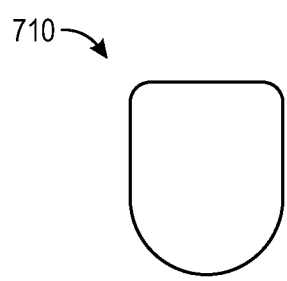
Figure 7D:
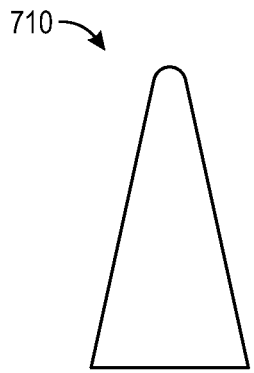
Figure 7E:
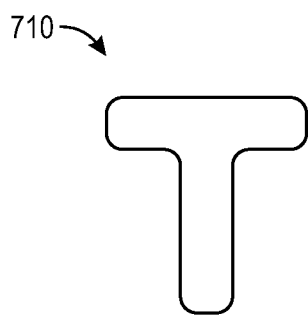
Figure 7F:
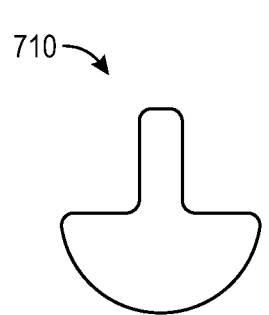
Figure 7G:
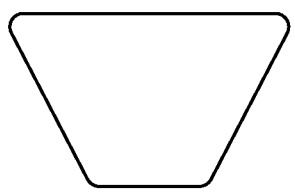
Figure 7H:
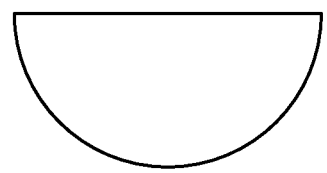
Figure 7I:
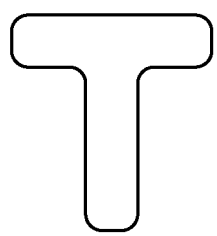
Figure 7J:
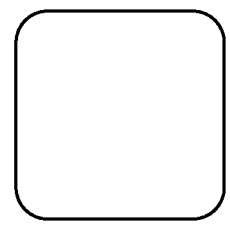
Figure 7K:
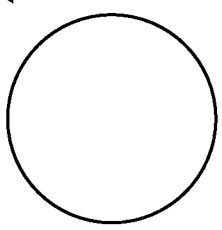
Figure 7L:
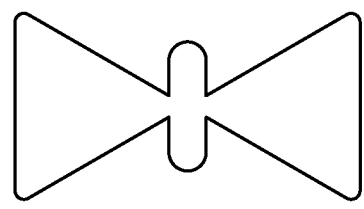

In some other embodiments, the valve repair device 200 can omit the stabilization member 220, the stabilization member 220 can have a different shape, and/or the number and position of the clip mechanisms 230 can be varied. For example, FIGS. 3A-3D are a front view, a side view, a rear view, and a top view, respectively, of the valve repair device 200 with the stabilization member 220 omitted in accordance with embodiments of the present technology. For example, FIGS. 4A-4D are a front view, a side view, a rear view, and a top view, respectively, of the valve repair device 200 including a flexible, generally-round stabilization member 420 in accordance with embodiments of the present technology. In the illustrated embodiment, the stabilization member 420 includes a frame 421 having a number of generally-circular rings attached to the coaptation member 210 at a portion of their perimeter to, for example, provide (i) radial flexibility while minimizing lateral flexibility and (ii) a target location for additional sequential fixation to stabilize the rings against the atrial wall. And, for example, FIGS. 5A and 5B are a side view and a rear view, respectively, of a valve repair device 500 including an elongate-curved stabilization member 520 extending from a coaptation member 510 in accordance with embodiments of the present technology. In the illustrated embodiment, the stabilization member 520 includes a frame 521 having two tall wireform or laser cut structures that curve to, for example, track the shape of and brace against an atrial wall. Further, the coaptation member 510 includes only a single, centrally-located clip mechanism 530 depending therefrom.

II. SELECTED EMBODIMENTS OF TRICUSPID VALVE REPAIR DEVICES INCLUDING COAPTATION MEMBERS

In general, tricuspid valve repair devices in accordance with the present technology can include a coaptation member having a shape (e.g., transverse cross-sectional shape, side cross-sectional shape, three-dimensional volumetric shape) and size (e.g., volume, area, cross-sectional dimension) selected to correspond with the natural shape of a coaptation line of the tricuspid valve to, for example, fill a leak between and/or provide a coaptation surface for one more native leaflets of the tricuspid valve. For example, all or a portion of the coaptation member can be positioned (e.g., centrally positioned) between the leaflets, or positioned with a bias toward one or more of the leaflets and/or the annulus of the tricuspid valve. The coaptation member can be positioned to primarily displace one or more of the leaflets and/or primarily to fill a commissural gap between two or more of the leaflets. The shape of the coaptation member can be selected to encourage leaflet coaptation, fill areas of regurgitation, fixate leaflets into clip mechanisms, provide a coaptation surface, facilitate native coaptation in areas not in contact with the implant device, and/or suppress native leaflet flail. For example, shapes that narrow in the coaptation zone may pull the leaflets together, increasing coaptation depth along the coaptation line and creating an annuloplasty effect. Conversely, shapes that widen along the coaptation zone can uniquely fill regurgitation spaces (e.g., clefts) in the distended tricuspid valve anatomy, further create coaptation redundancies, and/or fill space left by the native leaflets. In some embodiments, the slight annuloplasty effect of approximating the leaflets can combine with the coaptation redundancy of the coaptation member to create an overall more competent valve. In some embodiments, the size and/or orientation of the coaptation member can be adjusted by a delivery system used to deliver the tricuspid valve repair device before the delivery system is removed.

In some embodiments, the coaptation member can be shaped with an atrial to ventricular gradient—such as a taper or twist—configured to direct forward flow, minimize transvalvular gradient, maximize pressure recovery, promote native leaflet closure, and/or mimic the natural eddies of blood flow throughout the cardiac cycle. The coaptation member can be covered by (i) a fabric covering on a non-coapting face that facilitates ingrowth into the leaflets to provide robust long-term fixation, and (ii) a smooth, non-woven textile (e.g. ePTFE) covering on a coapting face that provides an atraumatic surface for coapting with the native leaflets. In some embodiments, the coaptation member can include foam under the fabric covering to provide for further atraumatic coaptation of leaflets against the coaptation member. The coaptation member can be supported by braided wire, superelastic nitinol stent-like frames, expanding sponge-like materials, polymer balloons, and/or other support structures.

More specifically, for example, FIGS. 6A-6H are transverse cross-sectional views (e.g., top or atrial views, bottom or ventricular views) of various coaptation members 610 in accordance with embodiments of the present technology. As shown in FIGS. 6A-6H, respectively, the coaptation member 610 can have a crescent shape, oval shape, elongated polygonal shape, triangular or asymmetrical hexagonal shape, semicircular shape, mushroom-like or umbrella-like shape, T-shape, and/or star shape (e.g., having three or more points). Similarly, FIGS. 7A-7L are side cross-sectional views (e.g., anterior-posterior views and/or commissure-commissure views) of various coaptation members 710 in accordance with embodiments of the present technology. As shown in FIGS. 7A-7L, respectively, the coaptation member 710 can have a triangular shape (e.g., isosceles triangular shape), curved or fin-like shape, oval shape, inverted-triangular shape, elongated T-shape, inverted umbrella-like shape, trapezoidal shape, semicircular shape, laterally-elongated T-shape, square shape, circular shape, or bow-tie-like shape (e.g., including a pair of trapezoidal portions extending from a central member). The various transverse cross-sectional and side cross-sectional shapes of the coaptation members 610 and 710 can be combined to form coaptation members of different shapes and sizes. Likewise, in other embodiments, coaptation members in accordance with the present technology can have other shapes.

Figure 8B:
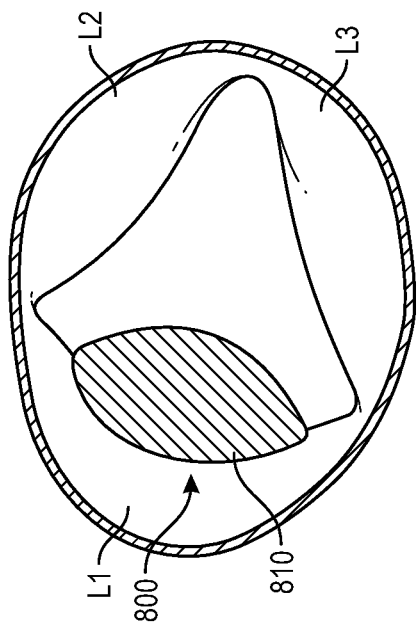
FIGS. 8B and 8C are transverse cross-sectional views of the valve repair device of FIG. 8A during diastole and systole, respectively, in accordance with embodiments of the present technology.
Figure 8C:
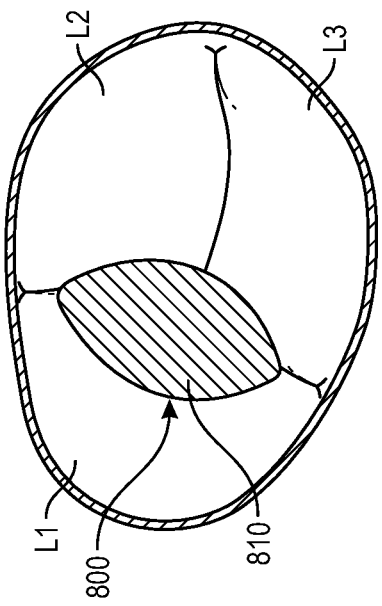
Figure 8A:
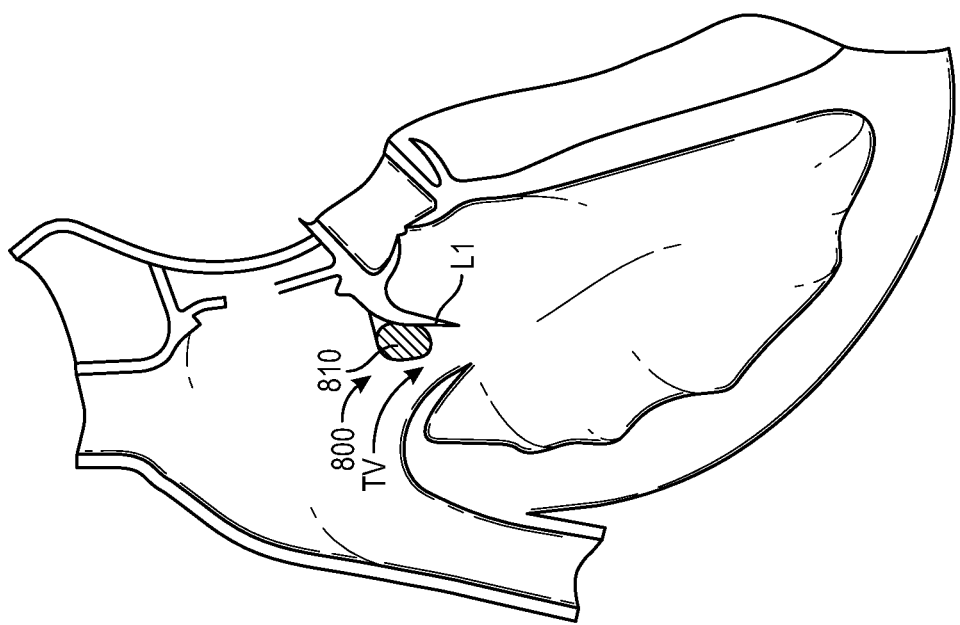
FIG. 8A is a side cross-sectional view of a valve repair device implanted at a tricuspid valve in accordance with embodiments of the present technology.

The various coaptation member shapes illustrated in FIGS. 6A-7L can be combined and/or modified based on, for example, the particular anatomy and/or abnormality of the tricuspid valve at which the valve repair device is to be implanted. For example, FIG. 8A is a side cross-sectional view of a valve repair device 800 implanted at a tricuspid valve TV in accordance with embodiments of the present technology. FIGS. 8B and 8C are transverse cross-sectional views of the valve repair device 800 of FIG. 8A during diastole and systole, respectively, in accordance with embodiments of the present technology. Referring to FIGS. 8A-8C together, the valve repair device 800 includes a coaptation member 810 having a generally circular side cross-sectional shape and an oval transverse cross-sectional shape. In the illustrated embodiment, the coaptation member 810 can be secured to and/or against a first leaflet L1 of the tricuspid valve TV, such as the posterior leaflet, via one or more clip mechanisms, anchors, and/or other securing features described herein (not shown). In other embodiments, the coaptation member 810 can additionally or alternatively be secured to and/or against a second leaflet L2 (e.g., the anterior leaflet) and/or a third leaflet L3 (e.g., the septal leaflet). The coaptation member 810 provides a coaptation surface for the second and third leaflets L2 and L3 as shown in, for example, FIG. 8C.

Figure 9B:
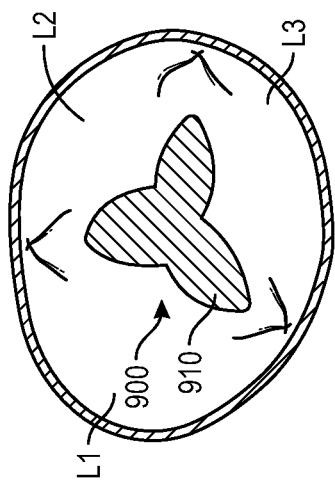
FIGS. 9B and 9C are transverse cross-sectional views of the valve repair device of FIG. 9A during diastole and systole, respectively, in accordance with embodiments of the present technology.
Figure 9C:
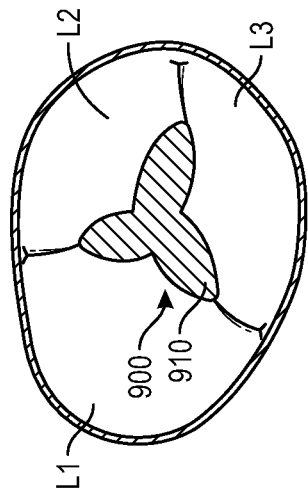
Figure 9D:
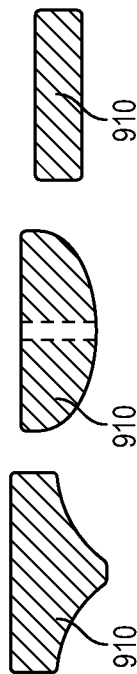
FIG. 9D includes several side cross-sectional views of a coaptation member of the valve repair device of FIGS. 9A-9C in accordance with embodiments of the present technology.
Figure 9A:
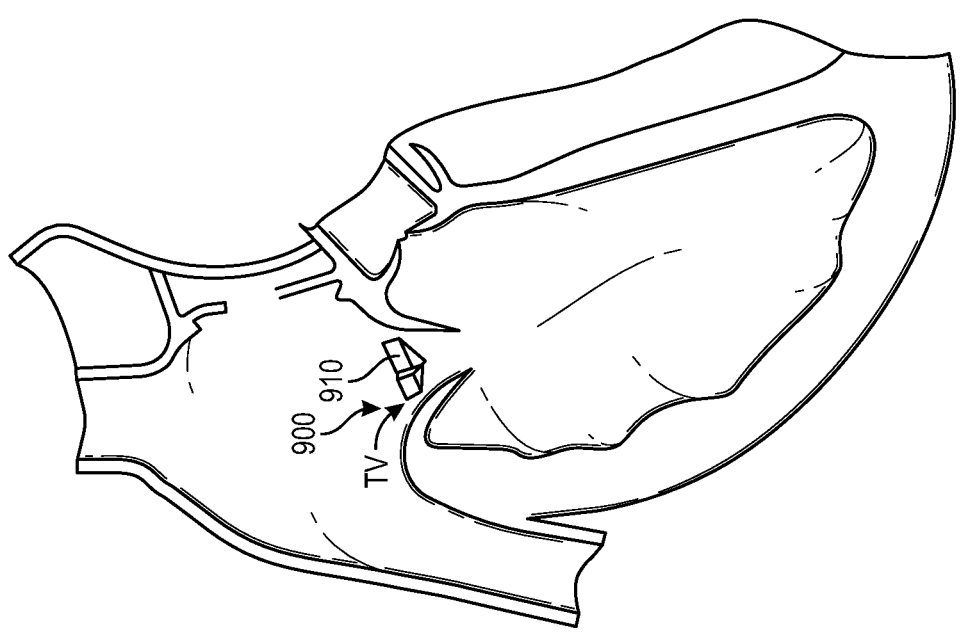
FIG. 9A is a side cross-sectional view of a valve repair device implanted at the tricuspid valve in accordance with embodiments of the present technology.

FIG. 9A is a side cross-sectional view of a valve repair device 900 implanted at the tricuspid valve TV in accordance with embodiments of the present technology. FIGS. 9B and 9C are transverse cross-sectional views of the valve repair device of FIG. 9A during diastole and systole, respectively, in accordance with embodiments of the present technology. Referring to FIGS. 9A-9C together, the valve repair device 900 includes a coaptation member 910 having a generally pentagonal side cross-sectional shape and a three-pointed-star-like transverse cross-sectional shape. In the illustrated embodiment, the valve repair device 900 can be secured between the leaflets L1-L3 of the tricuspid valve TV via one or more clip mechanisms, lock mechanisms, anchors, and/or other securing features described herein (not shown). As best seen in FIGS. 9B and 9C, the star-like transverse cross-sectional shape of the coaptation member 910 can be oriented such that each of the points of the star generally points toward a corresponding one of the commissures between the leaflets L1-L3 to, for example, facilitate the coaptation of the leaflets L1-L3 against the surface of the coaptation member 910. In other embodiments, the coaptation member 910 of the valve repair device 900 can have any of the side cross-sectional shapes shown in FIG. 9D including, for example, a curved-pentagonal, squared-semicircular, or rectangular shape.

Figure 10A:
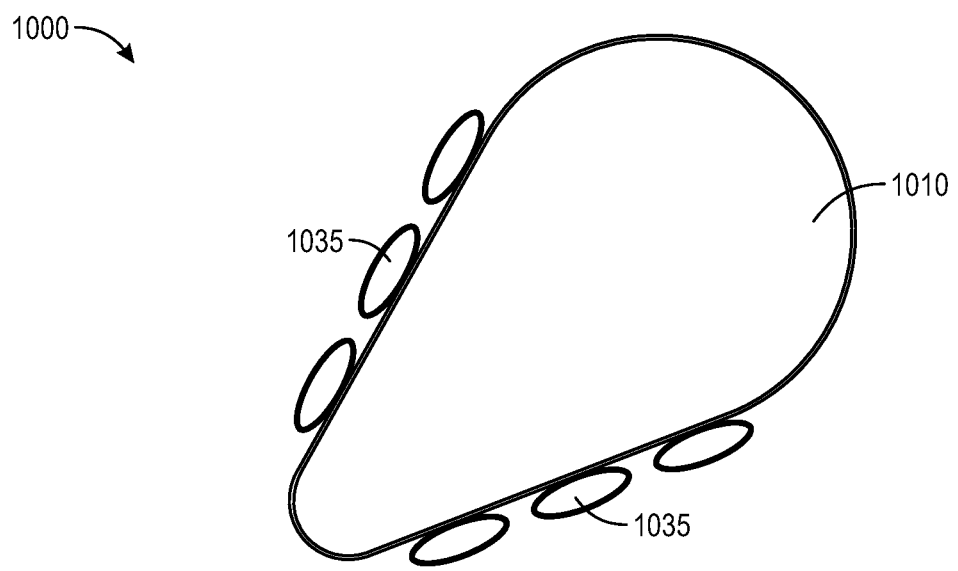
FIG. 10A is a top view of a valve repair device in accordance with embodiments of the present technology.
Figure 10C:
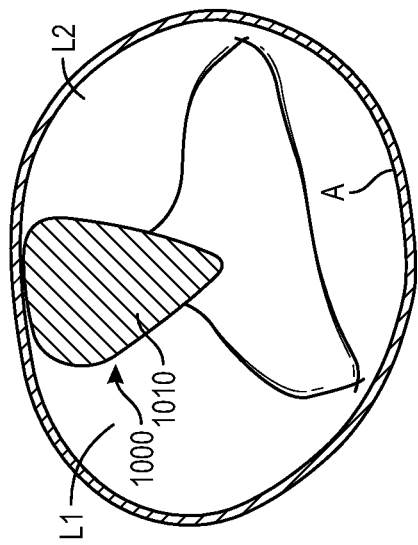
FIGS. 10C and 10D are transverse cross-sectional views of the valve repair device of FIGS. 10A and 10B during diastole and systole, respectively, in accordance with embodiments of the present technology.
Figure 10D:
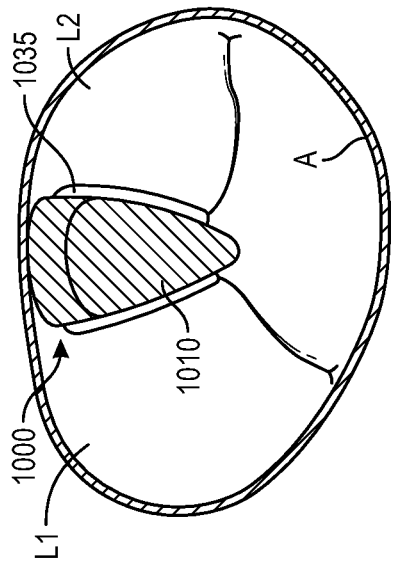
Figure 10B:
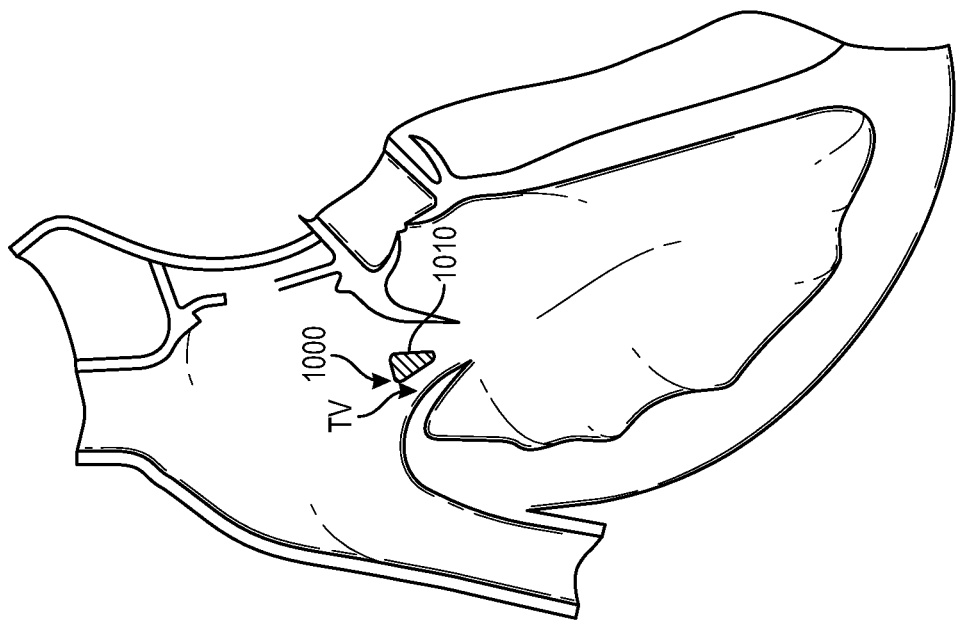
FIG. 10B is a side cross-sectional view of the valve repair device of FIG. 10A implanted at the tricuspid valve in accordance with embodiments of the present technology.

FIG. 10A is a top view of a valve repair device 1000 in accordance with embodiments of the present technology. FIG. 10B is a side cross-sectional view of the valve repair device 1000 of FIG. 10A implanted at the tricuspid valve TV in accordance with embodiments of the present technology. FIGS. 10C and 10D are transverse cross-sectional views of the valve repair device of FIGS. 10A and 10B during diastole and systole, respectively, in accordance with embodiments of the present technology. Referring to FIGS. 10A-10D together, the valve repair device 1000 includes a coaptation member 1010 with generally triangular (e.g., teardrop-shaped, ovoid-shaped) side and transverse cross-sectional shapes. The valve repair device 1000 further includes a fixation mechanism 1035 extending from one or more edges of coaptation member 1010 and configured to secure the coaptation member 1010 to two or more of the leaflets of the tricuspid valve, such as the leaflets L1 and L2 of the tricuspid valve TV. In other embodiments, the fixation mechanism 1035 can include one or more clip mechanisms, lock mechanisms, anchors, and/or other securing features described herein for fixating the device onto the leaflets of the valve. Accordingly, the coaptation member 1010 can (i) be positioned in the commissure between the leaflets, (ii) extend into the center of the tricuspid valve TV, and (iii) be shaped to fill a regurgitant orifice and prevent regurgitation. In some embodiments, the coaptation member 1010 can be biased toward an annulus A of the tricuspid valve TV to help fill a regurgitant space in the valve.

III. SELECTED EMBODIMENTS OF TRICUSPID VALVE REPAIR DEVICES INCLUDING MECHANISMS FOR SECURING TO CARDIAC ANATOMY GENERALLY LOCAL TO THE TRICUSPID VALVE

In some embodiments, cardiac valve repair devices in accordance with the present technology can include implant fixation mechanisms for securing the device into the local native anatomy of the tricuspid valve by, for example, anchoring into or laying against the native ventricular wall, against the annulus, and/or onto the leaflets themselves. In some embodiments, the implant fixation mechanisms can include one or more clip mechanisms and one or more lock mechanisms. The clip mechanisms (also referred to as "clips," "capture clips," "capture mechanisms," and iterations thereof) are configured to be positioned on the ventricular side of the tricuspid valve and to capture one or more leaflets of the valve for securing the leaflets against, for example, a coaptation member coupled to the clip mechanisms and lock mechanisms. The lock mechanisms (also referred to as "clips," "locking clips," "stabilization members," "stabilization features", and iterations thereof) can be generally similar to the clip mechanisms but are configured to be positioned on the atrial side of the tricuspid valve and to engage the atrial side of the valve leaflets and/or other portions of the cardiac anatomy to, for example, help secure the coaptation member in a selected position relative to the tricuspid valve and/or provide additional leaflet fixation. The clip and lock mechanisms may or may not require a specific orientation and can be interchanged in functionality.

In some embodiments, the clip mechanisms can be on (i) opposing sides of the coaptation member, (ii) one side of the coaptation member, and/or (iii) a mating surface inferior to the coaptation member. In some embodiments, the clip mechanisms and/or the lock mechanisms can be movable, expandable, and/or otherwise adjustable. In some embodiments, the clip mechanisms can be narrow numerate features configured to navigate chordae proximate to the tricuspid valve and/or to minimize leaflet disruption during diastole (e.g., allowing forward flow), and the lock mechanisms can be wide features on the atrial side to minimize leaflet flail and provide additional flow resistance during systole. In some embodiments, the clip and lock mechanisms can operate independently from one another and can be repositionable. Further, the clip and lock mechanisms (e.g., arms thereof) can (i) have various shapes supporting the native leaflet shapes, (ii) be set at an angle to mimic the natural leaflet coaptation angle, and/or (iii) be configured to capture only the free edge of one or more of the leaflets.

In some embodiments, the implant fixation mechanisms can include features configured to enhance leaflet fixation, such as (i) interlocking components configured to increase leaflet plication, (ii) materials or features that increase surface area in contact with the leaflets, (iii) frictional elements (e.g., cleats, barbs, textures) that increase friction against the leaflets, (iv) features that puncture the leaflets, and/or (v) combinations thereof. For tricuspid valve repair devices having clips on the atrial and ventricular sides of the device, features on the atrial side of the leaflet (e.g., lock mechanisms) may fit within the spacing of the sub-valvular features. Fixation features can be gear driven, hydraulic, superelastic, or spring-loaded. Features that contact the leaflet can be widened to distribute the closing force across a wider area. Some stabilizing features can utilize flared, angled, or wide fixation mechanisms to add stability to the device and facilitate the natural coaptation angle of the native valve. In some embodiments, the clip mechanisms and/or the lock mechanisms can include a patent foramen ovale (PFO) closure device configured as an atrial anchor.

In some embodiments, the clip mechanisms and/or the lock mechanisms can be in the form of a hook so as to not tightly pull the leaflet up against the coaptation member but to just approximate it. This configuration can allow for a captured leaflet to open more during diastole thereby reducing pressure gradients. When multiple (e.g., two) ventricular clip mechanisms are in the form of hooks, atrial annular support and/or anchor members can be included to inhibit migration of the device into the ventricle. In some embodiments, the atrial anchors can be inserted into the septal wall through a stabilizing member connected to the coaptation member. In some embodiments, the clip mechanisms can include one or more clip expandable arms that work efficiently in treating a wide mitral regurgitation jet without the need for a coaptation member with a C—C protrusion.

Figure 11B:
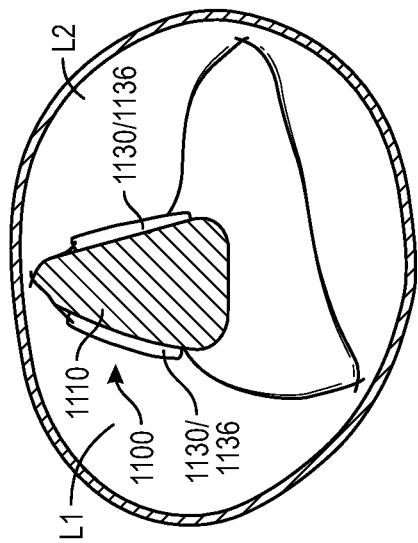
FIGS. 11B and 11C are transverse cross-sectional views of the valve repair device of FIG. 11A during diastole and systole, respectively, in accordance with embodiments of the present technology.
Figure 11C:
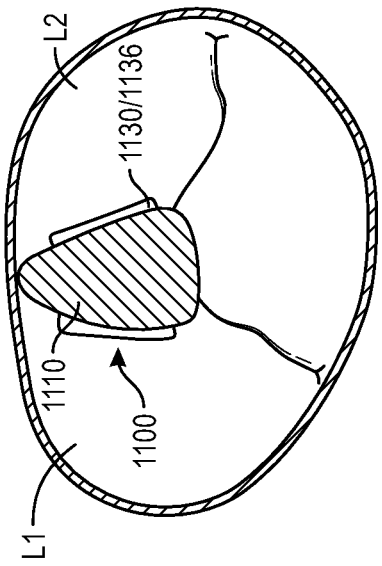
Figure 11A:
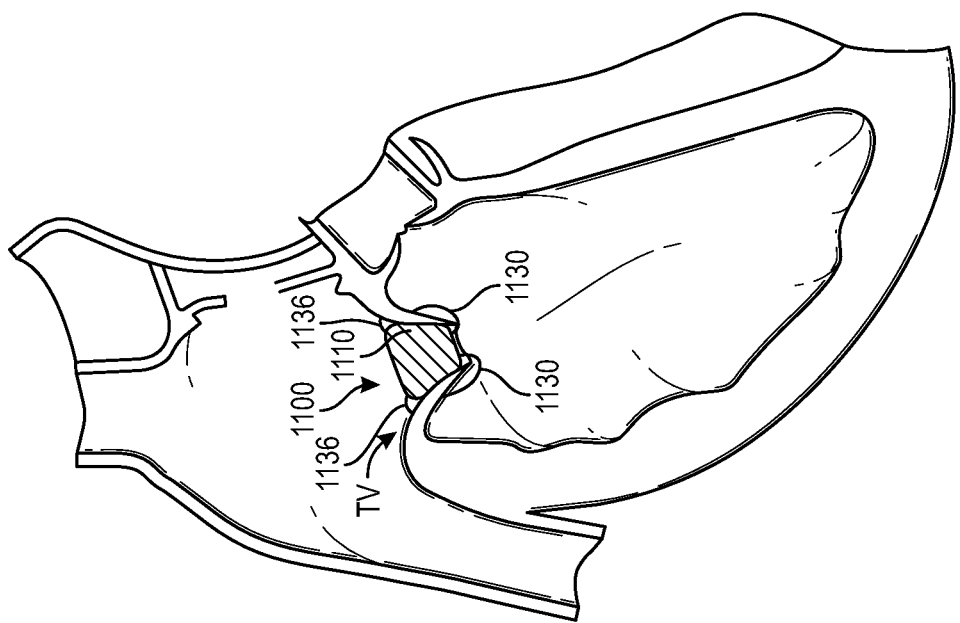
FIG. 11A is a side cross-sectional view of a valve repair device implanted at the tricuspid valve in accordance with embodiments of the present technology.

FIG. 11A is a side cross-sectional view of a valve repair device 1100 implanted at the tricuspid valve TV in accordance with embodiments of the present technology. FIGS. 11B and 11C are transverse cross-sectional views of the valve repair device 1100 of FIG. 11A during diastole and systole, respectively, in accordance with embodiments of the present technology. Referring to FIGS. 11A-11C together, the valve repair device includes features generally similar to the valve repair device 1000 of FIGS. 10A-10D including, for example, a coaptation member 1110 secured to the leaflets L1 and L2. In the illustrated embodiment, however, the coaptation member 1110 has a fixation mechanism including (i) clip mechanisms 1130 configured to engage the ventricular sides of the leaflets L1 and L2 and (ii) lock mechanisms 1136 configured to engage the atrial side of the leaflets L1 and L2. In addition, the coaptation member 1110 orientation has been reversed from the valve repair devices 1000 of FIGS. 10A-10D with the narrow portion of the surface of the coaptation member 1110 oriented towards the commissure between the leaflets. Accordingly, in some aspects of the present technology the coaptation member 1110 can be oriented and/or placed in versatile manner between the leaflets. In general, the various coaptation members of the present technology can be optionally placed in different orientations depending on the specific application of the valve and valve repair device.

Figure 12B:
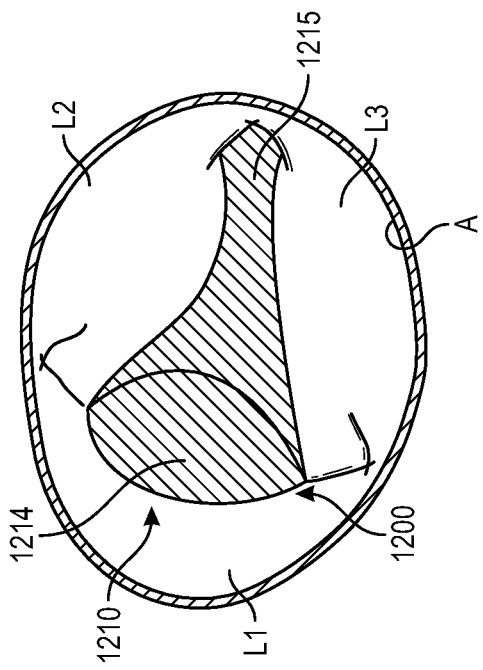
FIGS. 12B and 12C are transverse cross-sectional views of the valve repair device of FIG. 12A during diastole and systole, respectively, in accordance with embodiments of the present technology.
Figure 12C:
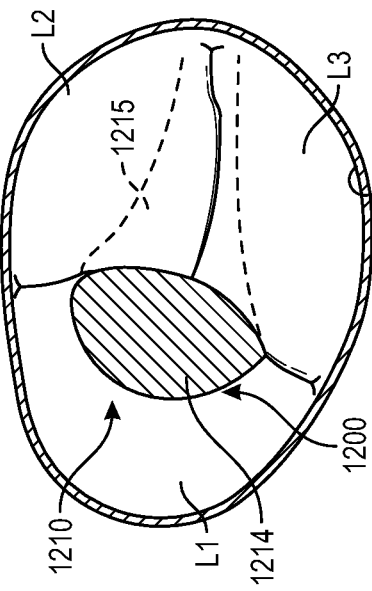
Figure 12A:
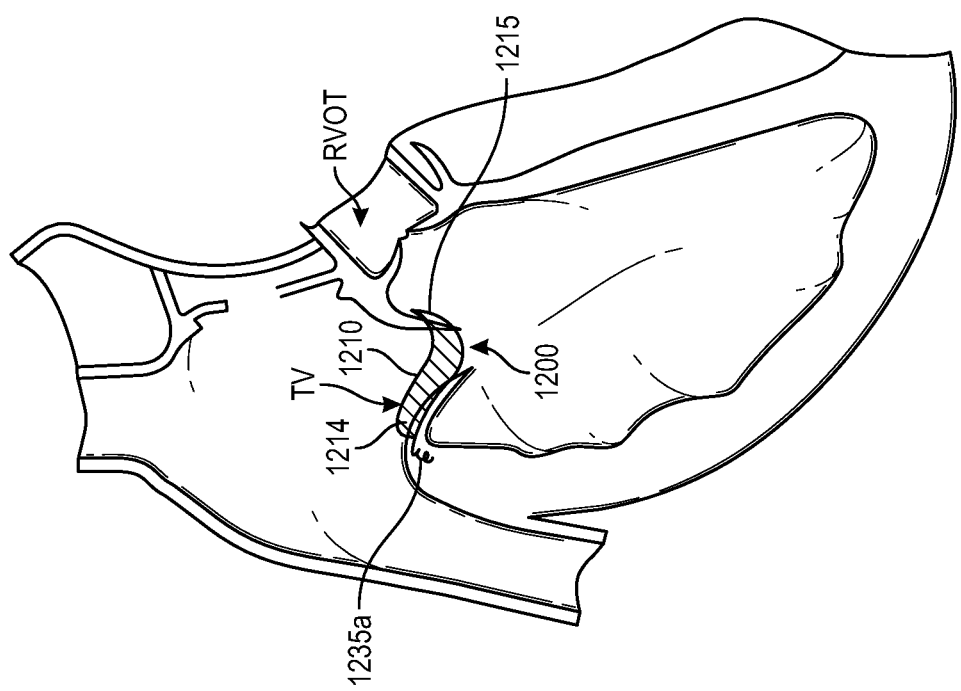
FIG. 12A is a side cross-sectional view of a valve repair device implanted at the tricuspid valve in accordance with embodiments of the present technology.

FIG. 12A is a side cross-sectional view of a valve repair device 1200 implanted at the tricuspid valve TV in accordance with embodiments of the present technology. FIGS. 12B and 12C are transverse cross-sectional views of the valve repair device of FIG. 12A during diastole and systole, respectively, in accordance with embodiments of the present technology. Referring to FIGS. 12A-12C together, the valve repair device 1200 includes a coaptation member 1210 with a generally elongated-triangular shape (e.g., a "bicycle-seat" shape). The coaptation member 1210 can further include (i) a supra-valvular portion 1214 secured (e.g., anchored) to the annulus A and/or one or more of the leaflets of the tricuspid valve TV via a first fixation mechanism 1235*a* and (ii) a sub-valvular portion 1215 anchored to one or more of the leaflets of the tricuspid valve TV via second fixation mechanism (not shown). In some embodiments, the first fixation mechanism 1235*a* can be an anchor, such as a helical screw, and the second fixation mechanism can be a clip mechanism. Accordingly, the coaptation member 1210 can replace all or part of a native leaflet of the tricuspid valve TV (e.g., the leaflet L1) while providing a coaptation surface for one or more of the other native leaflets (e.g., the leaflets L2 and L3). In other embodiments, the second fixation mechanism can additionally or alternatively include an anchor or hook feature configured to secure the sub-valvular portion 1215 of the coaptation member 1210 to a portion of the cardiac anatomy at or near a right ventricular outflow tract RVOT.

Figure 13B:
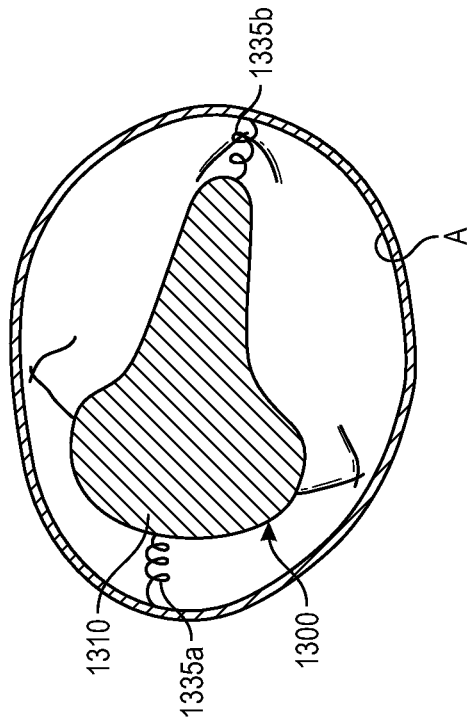
FIGS. 13B and 13C are transverse cross-sectional views of the valve repair device of FIG. 13A during diastole and systole, respectively, in accordance with embodiments of the present technology.
Figure 13C:
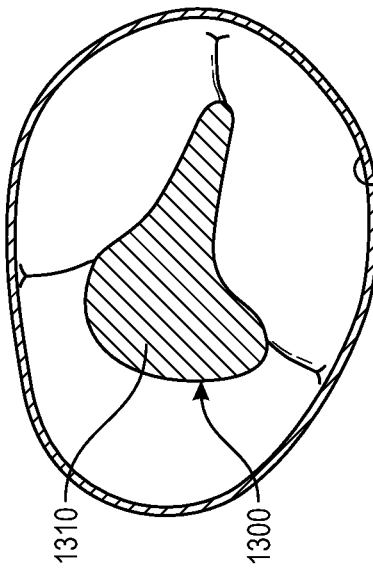
Figure 13A:
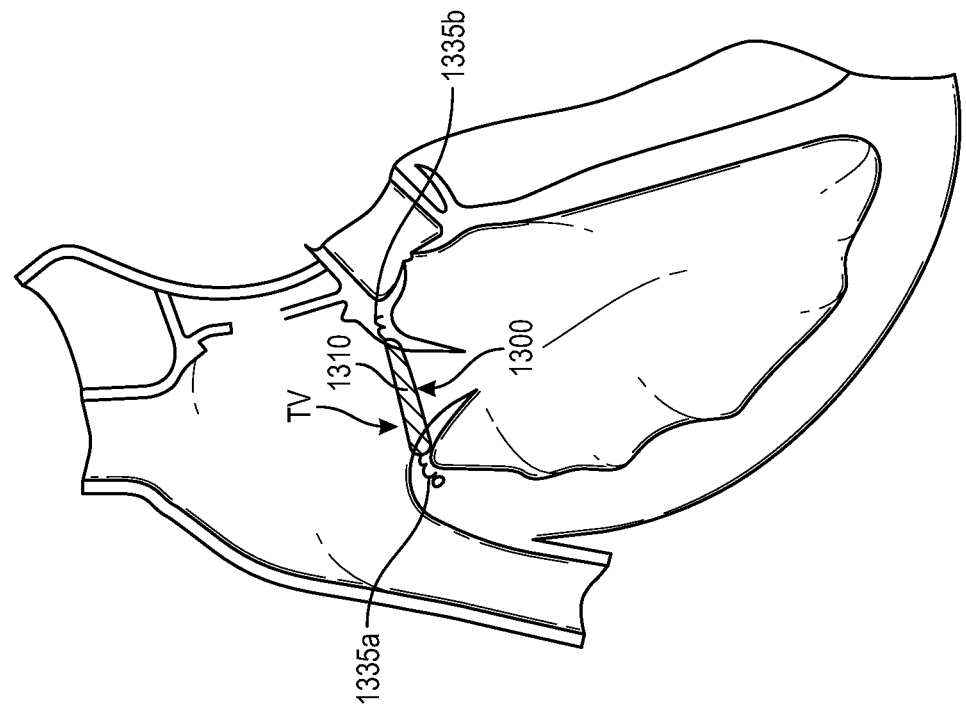
FIG. 13A is a side cross-sectional view of a valve repair implanted at the tricuspid valve in accordance with embodiments of the present technology.

In yet other embodiments, the second fixation mechanism can be an anchor (e.g., a second helical screw) configured to secure the coaptation member to the annulus A of the tricuspid valve TV. For example, FIG. 13A is a side cross-sectional view of a valve repair device 1300 similar to FIGS. 12A-12C implanted at the tricuspid valve TV with a first fixation mechanism 1335a and a second fixation mechanism 1335b anchoring the coaptation member 1310 to the annulus A in accordance with embodiments of the present technology. FIGS. 13B and 13C are transverse cross-sectional views of the valve repair device 1300 of FIG. 13A during diastole and systole, respectively, in accordance with embodiments of the present technology. Referring to FIGS. 13A-13C, the second fixation mechanism 1335b can be secured to the annulus A such that most or all of the coaptation member 1310 is positioned at the coaptation surface of the tricuspid valve TV.

Figure 14A:
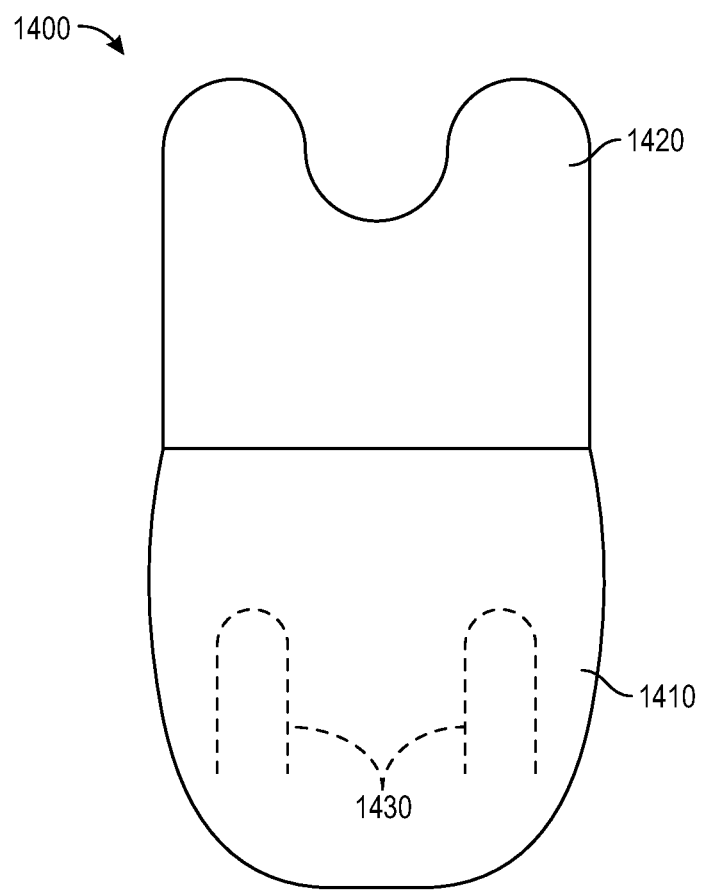
FIG. 14A is a front view of a tricuspid valve repair device in accordance with embodiments of the present technology.
Figure 14C:
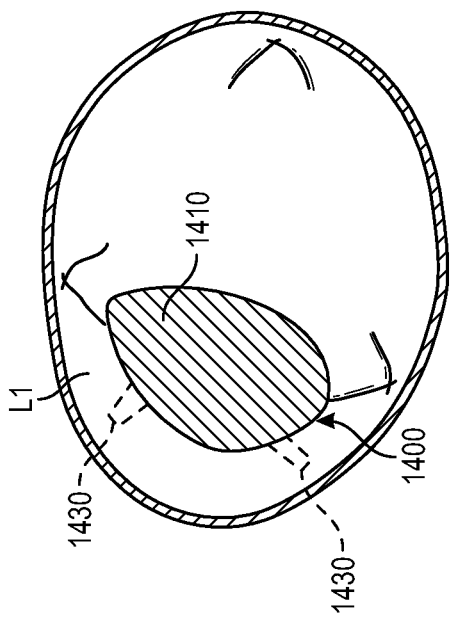
FIGS. 14C and 14D are transverse cross-sectional views of the valve repair device of FIGS. 14A and 14B during diastole and systole, respectively, in accordance with embodiments of the present technology.
Figure 14D:
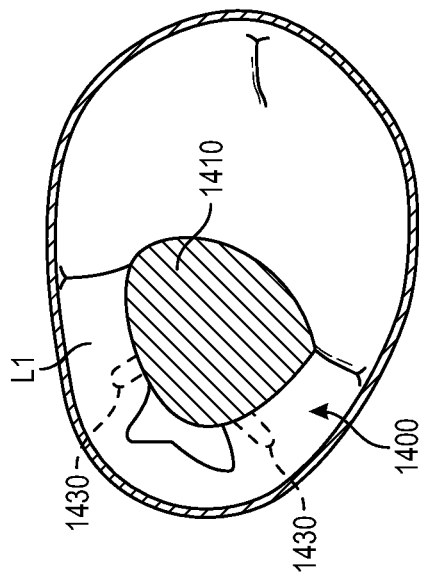
Figure 14B:
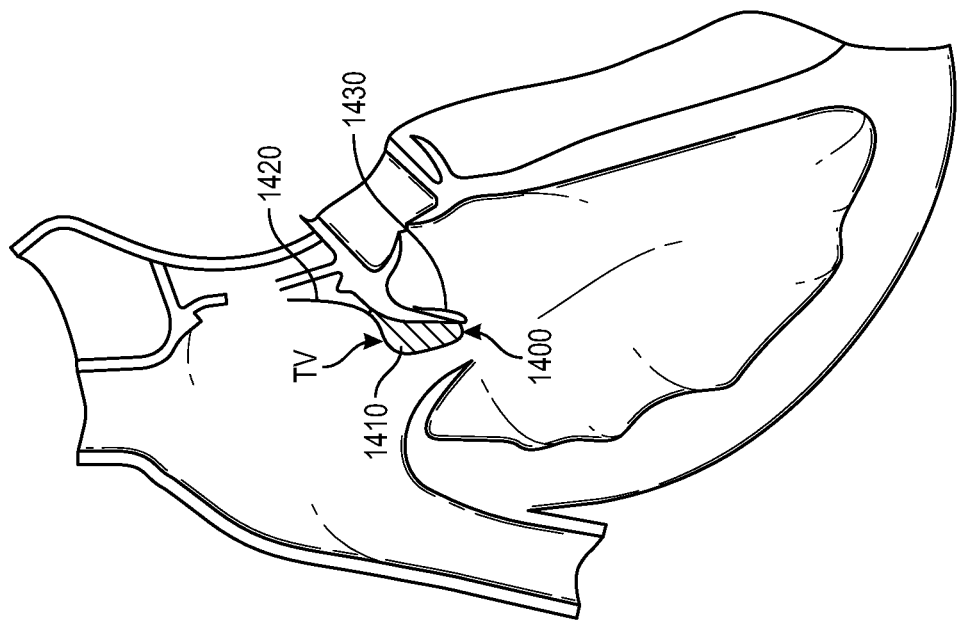
FIG. 14B is a side cross-sectional view of the valve repair device of FIG. 14A implanted at the tricuspid valve in accordance with embodiments of the present technology.

FIG. 14A is a front view of a tricuspid valve repair device 1400 in accordance with embodiments of the present technology. FIG. 14B is a side cross-sectional view of the valve repair device 1400 of FIG. 14A implanted at the tricuspid valve TV in accordance with embodiments of the present technology. FIGS. 14C and 14D are transverse cross-sectional views of the valve repair device 1400 of FIGS. 14A and 14B during diastole and systole, respectively, in accordance with embodiments of the present technology. Referring to FIGS. 14A-14D together, the valve repair device 1400 can include features generally similar or identical to those of the tricuspid valve repair device 200 of FIGS. 2A-2D including, for example, (i) a coaptation member 1410 having a pair of clip mechanisms 1430 coupled thereto and (ii) a stabilization member 1420 (also referred to as an atrial support member) extending upward away from the coaptation member 1410. The stabilization member 1420 is configured to anchor or brace against the septal wall above the tricuspid valve TV, as best seen in FIG. 14B, to help secure the position of the coaptation member 1410 between the native leaflets. The stabilization member 1420 can also provide a platform for tissue ingrowth and long-term fixation. Additionally, the stabilization member 1420 can serve as platform to locate supplemental anchors into the atrial septum. The clip mechanisms 1430 can secure (e.g., fix) the coaptation member 1410 to one of the native leaflets (e.g., the leaflet L1; the septal leaflet) such that the coaptation member 1410 replaces all or part the leaflet L1 and provides a coaptation surface for one or more of the other native leaflets.

Figure 14E:
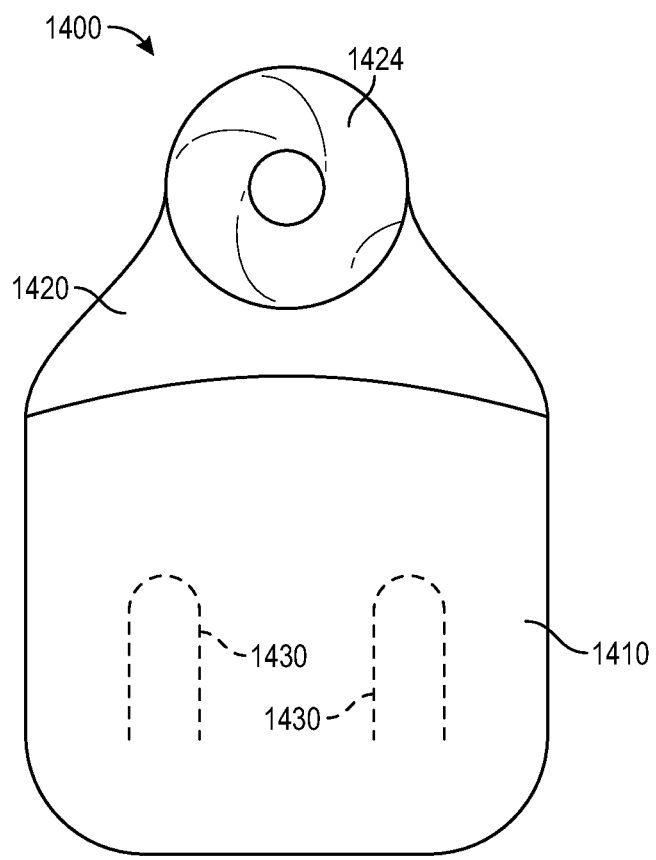
FIG. 14E is a front view of the tricuspid valve repair device of FIGS. 14A-14D in accordance with additional embodiments of the present technology.

In some embodiments, the stabilization member 1420 is configured to puncture the septal wall to further stabilize the coaptation member 1410 at the tricuspid valve TV. For example, FIG. 14E is a front view of the valve repair device 1400 of FIGS. 14A-14D including a puncture feature 1424 on the stabilization member 1420 in accordance with embodiments of the present technology. The puncture feature 1424 is configured to puncture the septal wall to fixate the stabilization member 1420 thereto.

Figure 15A:
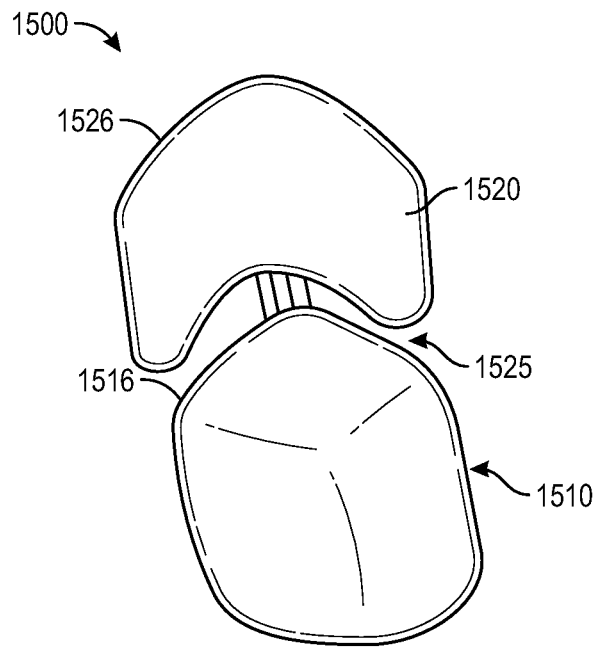
FIG. 15A is a top view of a valve repair device in accordance with embodiments of the present technology.
Figure 15B:
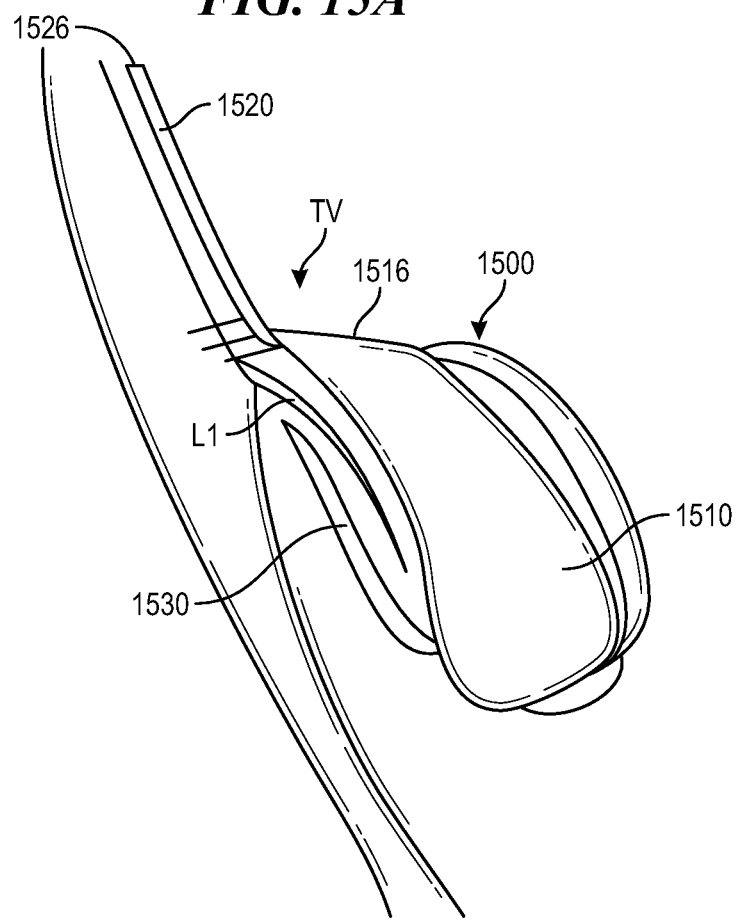
FIG. 15B is a side cross-sectional view of the valve repair device of FIG. 15A implanted at the tricuspid valve in accordance with embodiments of the present technology.

FIG. 15A is a top view of a valve repair device 1500 in accordance with embodiments of the present technology. FIG. 15B is a side cross-sectional view of the valve repair device 1500 of FIG. 15A implanted at the tricuspid valve TV in accordance with embodiments of the present technology. Referring to FIGS. 15A and 15B together, the valve repair device 1500 includes a coaptation member 1510 (also referred to as a "baffle"), a stabilization member 1520 (also referred to as a "chair-back") extending from the coaptation member 1510, and a clip mechanism 1530 extending from the coaptation member 1510. The stabilization member 1520 can engage an atrial or septal wall above the tricuspid valve TV to help stabilize the position of the coaptation member 1510 between one or more native leaflets of the tricuspid valve TV. The clip mechanism 1530 can engage the leaflet L1 to secure the coaptation member 1510 against the leaflet L1. In some embodiments, the stabilization member 1520 is positioned against the septal wall between the right atrium and the left atrium and the leaflet L1 is the septal leaflet of the tricuspid valve TV.

In the illustrated embodiment, the stabilization member 1520 is spaced apart from the coaptation member 1510 by a gap 1525 (FIG. 15A) to, for example, enable the coaptation member 1510 to be deployed from a delivery system and tested before deploying the stabilization member 1520 from the delivery system. The stabilization member 1520 may be connected to the coaptation member 1510 through sutures and fabric, small superelastic wires, and/or other attachment mechanisms to, for example, maintain independence and flexibility while providing stabilization. In some embodiments, a top portion 1516 of the coaptation member 1510 and a top portion 1526 of the stabilization member 1520 can each have a triangular, angled, or "chevron-like" shape to, for example, enable to the valve repair device 1500 to be more easily recaptured or recovered into the delivery system.

Figure 16B:
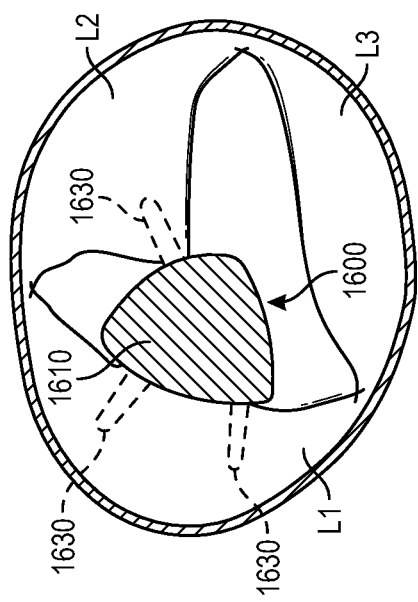
FIGS. 16B and 16C are transverse cross-sectional views of the valve repair device of FIG. 16A during diastole and systole, respectively, in accordance with embodiments of the present technology.
Figure 16C:
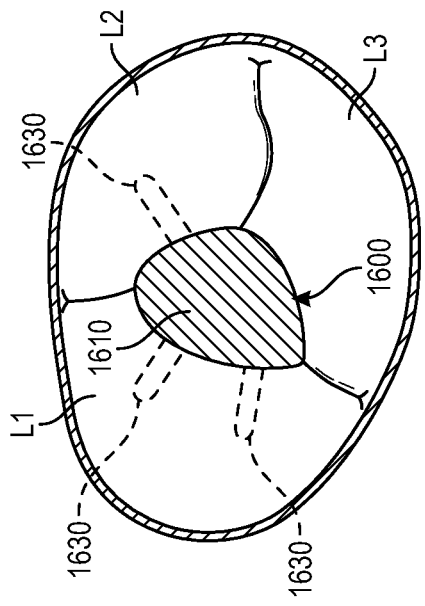
Figure 16A:
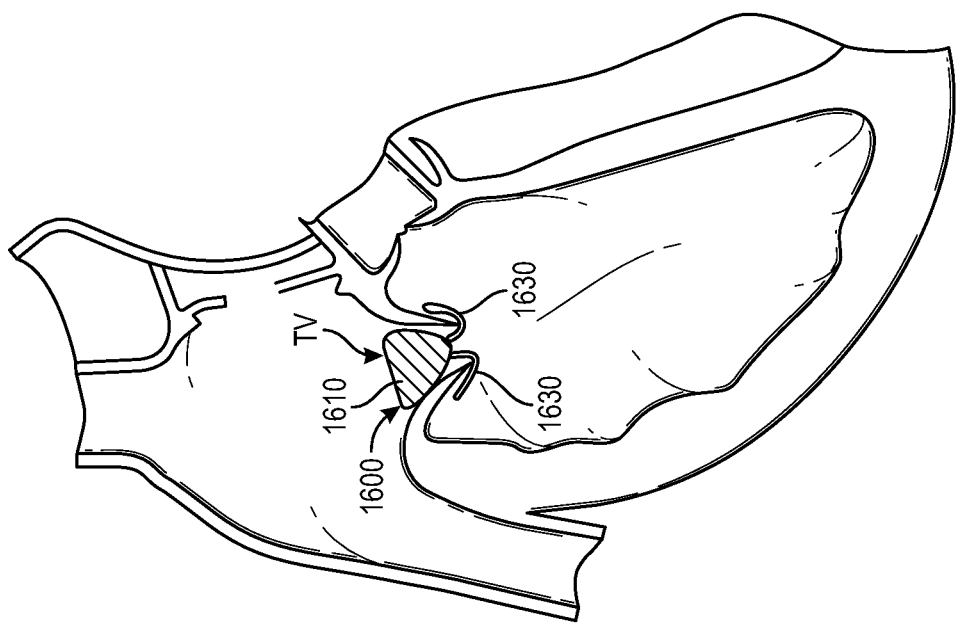
FIG. 16A is a side cross-sectional view of a valve repair device implanted at the tricuspid valve in accordance with embodiments of the present technology.

FIG. 16A is a side cross-sectional view of a valve repair device 1600 implanted at the tricuspid valve TV in accordance with embodiments of the present technology. FIGS. 16B and 16C are transverse cross-sectional views of the valve repair device 1600 of FIG. 16A during diastole and systole, respectively, in accordance with embodiments of the present technology. Referring to FIGS. 16A-16C together, the valve repair device 1600 includes a coaptation member 1610 and a plurality of clip mechanisms 1630 configured to secure the coaptation member 1610 to two or more of the native leaflets of the tricuspid valve TV. In the illustrated embodiment, for example, two of the clip mechanisms 1630 fix the coaptation member to the leaflet L1 (e.g., the septal leaflet) and one of the clip mechanisms 1630 fixes the coaptation member to the leaflet L2 (e.g., the anterior or posterior leaflet) to allow the remaining leaflet L3 (e.g., the other of the anterior or posterior leaflet) to coapt freely against the surface of the coaptation member 1610. In some embodiments, the coaptation member 1610 can be shaped to fill the resultant gap between the leaflets L1-L3. For example, the coaptation member 1610 can have both a generally rounded-triangular transverse cross-sectional shape and side cross-sectional shape as shown in FIGS. 16A-16C.

Figure 17B:
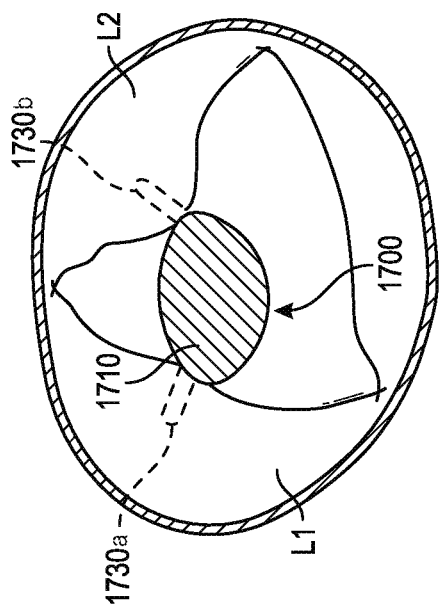
FIGS. 17B, 18B, and 19B are transverse cross-sectional views of the valve repair devices of FIGS. 17A, 18A, and 19A, respectively, during diastole in accordance with embodiments of the present technology.
Figure 17C:
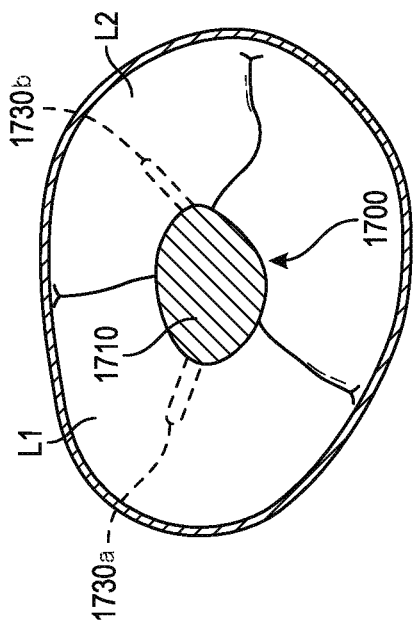
FIGS. 17C, 18C, and 19C are transverse cross-sectional views of the valve repair devices of FIGS. 17A, 18A, and 19A, respectively, during systole in accordance with embodiments of the present technology.
Figure 17A:
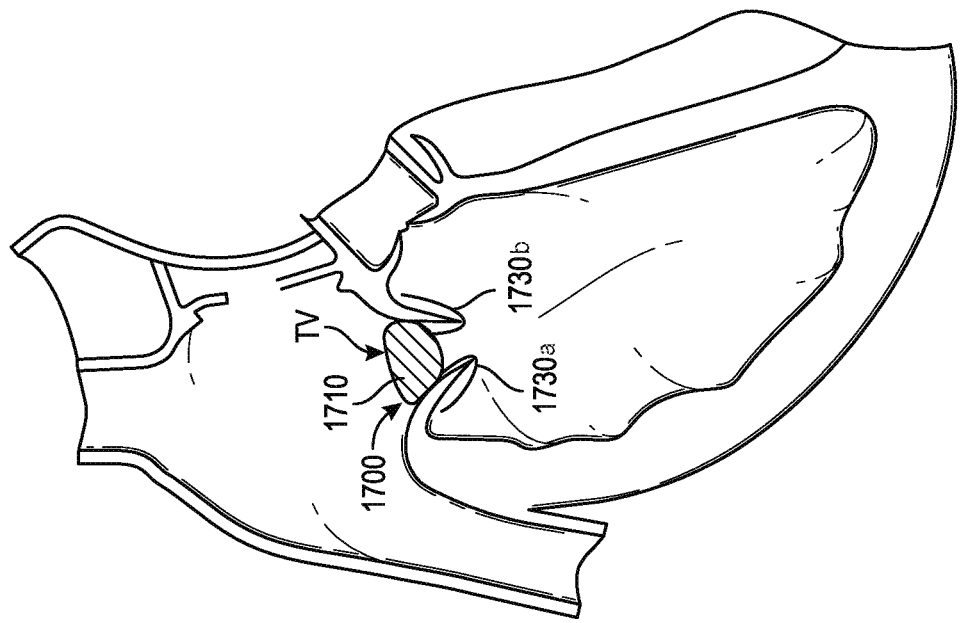
FIGS. 17A, 18A, and 19A are side cross-sectional view of valve repair devices implanted at the tricuspid valve in accordance with embodiments of the present technology.
Figure 18B:
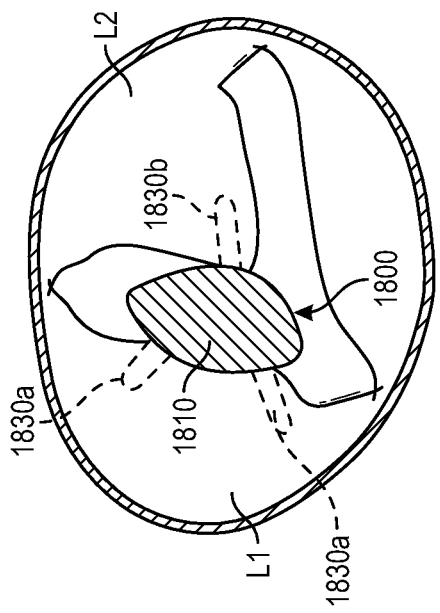
Figure 18C:
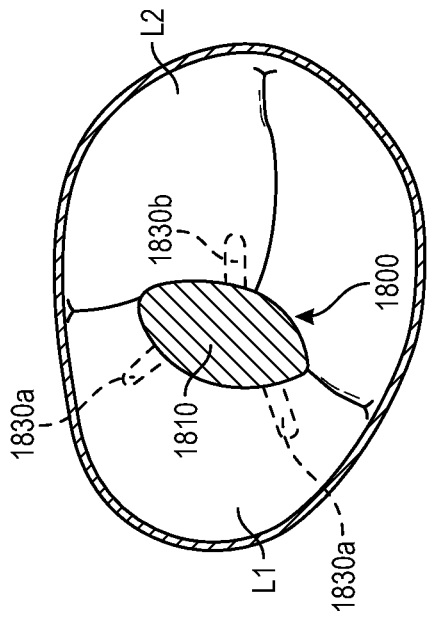
Figure 18A:
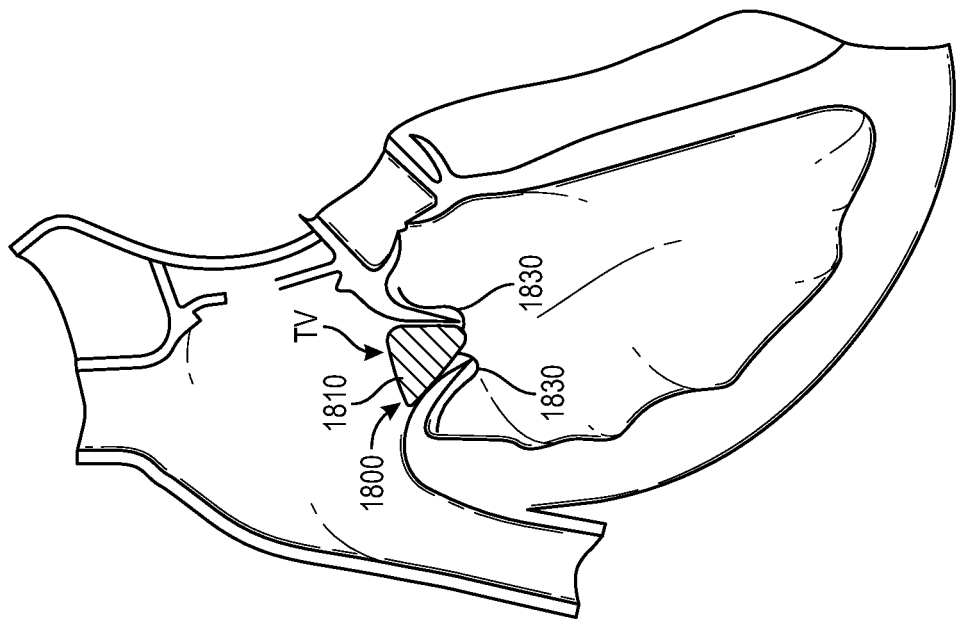
Figure 19B:
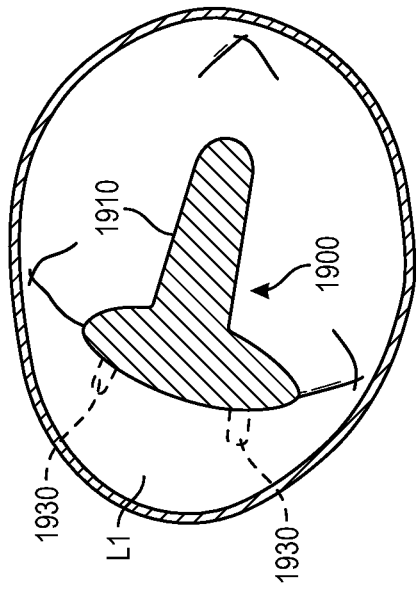
Figure 19C:
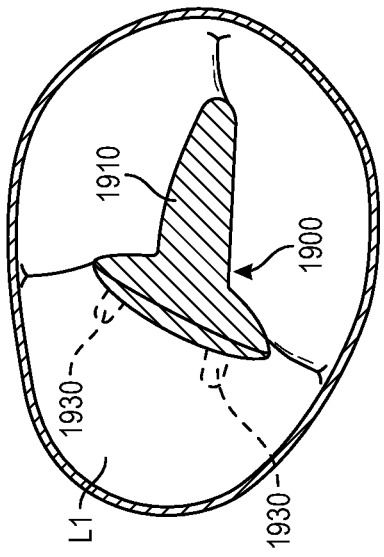
Figure 19A:
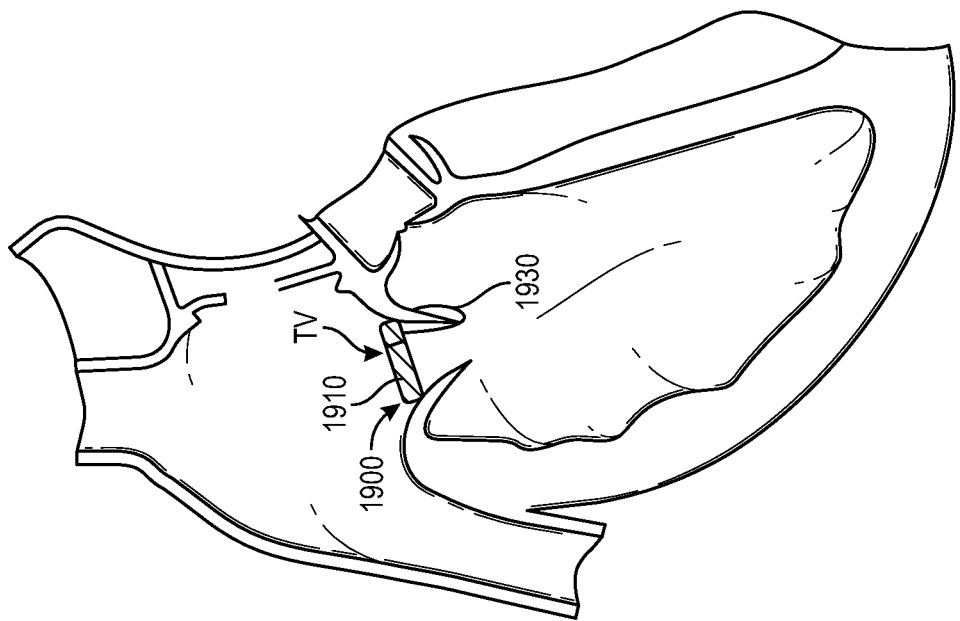

In other embodiments, a coaptation member of a valve repair device can have other shapes and/or the number and/or positioning of the clip mechanisms can vary. For example, FIGS. 17A, 18A, and 19A are side cross-sectional view of valve repair devices 1700, 1800, and 1900, respectively, implanted at the tricuspid valve TV in accordance with additional embodiments of the present technology. FIGS. 17B, 18B, and 19B are transverse cross-sectional views of the valve repair devices 1700, 1800, and 1900 of FIGS. 17A, 18A, and 19A, respectively, during diastole in accordance with embodiments of the present technology. And, FIGS. 17C, 18C, and 19C are transverse cross-sectional views of the valve repair devices 1700, 1800, and 1900 of FIGS. 17A, 18A, and 19A, respectively, during systole in accordance with embodiments of the present technology. Referring first to FIGS. 17A-17C together, the valve repair device 1700 can include (i) a coaptation member 1710 having a generally rounded-triangular or rounded-trapezoidal side cross-sectional shape and an almond or oval transverse cross-sectional shape, (ii) a first clip mechanism 1730a configured to fix the coaptation member 1710 to the leaflet L1, and (ii) a second clip mechanism 1730b configured to fix the coaptation member 1710 to the leaflet L2. Referring next to FIGS. 18A-18C together, the valve repair device 1800 can include (i) a coaptation member 1810 having a generally triangular side cross-sectional shape and an almond or oval transverse cross-sectional shape and (ii) a pair of first clip mechanisms 1830a configured to secure the coaptation member 1810 to the leaflet L1 and a single second clip mechanism 1830b configured to secure the coaptation member 1810 to the leaflet L2. Referring next to FIGS. 19A-19C together, the valve repair device 1900 can include (i) a coaptation member 1910 having a rectangular side cross-sectional shape and a bicycle-seat-like transverse cross-sectional shape and (ii) a pair of clip mechanisms 1930 configured to secure the coaptation member 1910 to the leaflet L1. Referring to FIGS. 17A-19C together, the coaptation members 1710, 1810, and/or 1910 may be shaped per any of the shapes illustrated in FIGS. 6A-6H and to extend through the tricuspid valve TV such that at least a portion of the coaptation member has a sub-valvular position in order to provide a coaptation surface across a range of valve etiologies and redundancies.

IV. SELECTED EMBODIMENTS OF TRICUSPID VALVE REPAIR DEVICES INCLUDING MECHANISMS FOR SECURING TO CARDIAC ANATOMY GENERALLY REMOTE FROM THE TRICUSPID VALVE

In some embodiments, a tricuspid valve repair device in accordance with embodiments of the present technology can include (i) a coaptation member positioned between the native valve leaflets, and (ii) one or more anchors, tethers, and/or support members that additionally or alternatively secure the coaptation member to anatomy of the heart other than the native leaflets, annulus, or other local anatomy of the tricuspid valve. For example, the anchors can be secured to the right atrial wall, right ventricular wall, right ventricular outflow tract, inferior vena cava, superior vena cava, and/or other portions of the anatomy of the right heart of the patient.

Figure 20B:
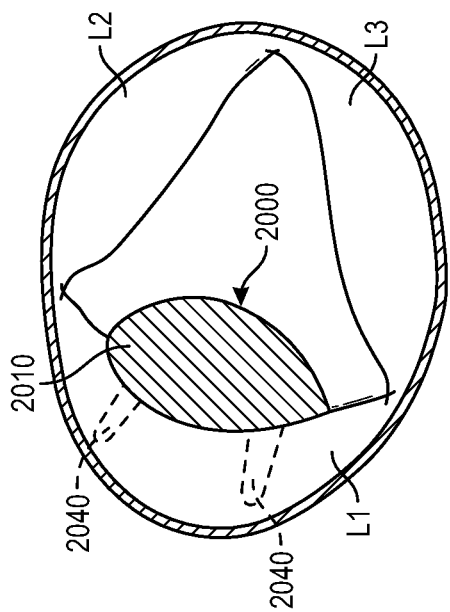
FIGS. 20B and 20C are transverse cross-sectional views of the valve repair device of FIG. 20A during diastole and systole, respectively, in accordance with embodiments of the present technology.
Figure 20C:
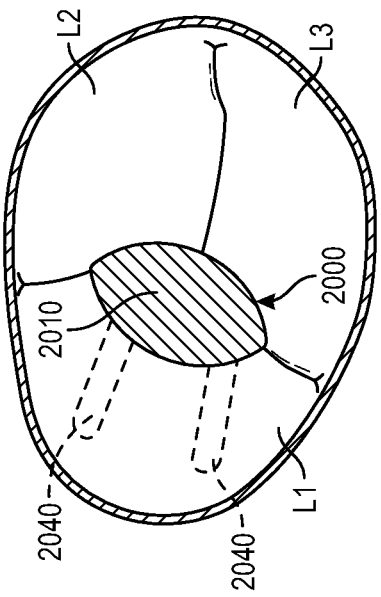
Figure 20A:
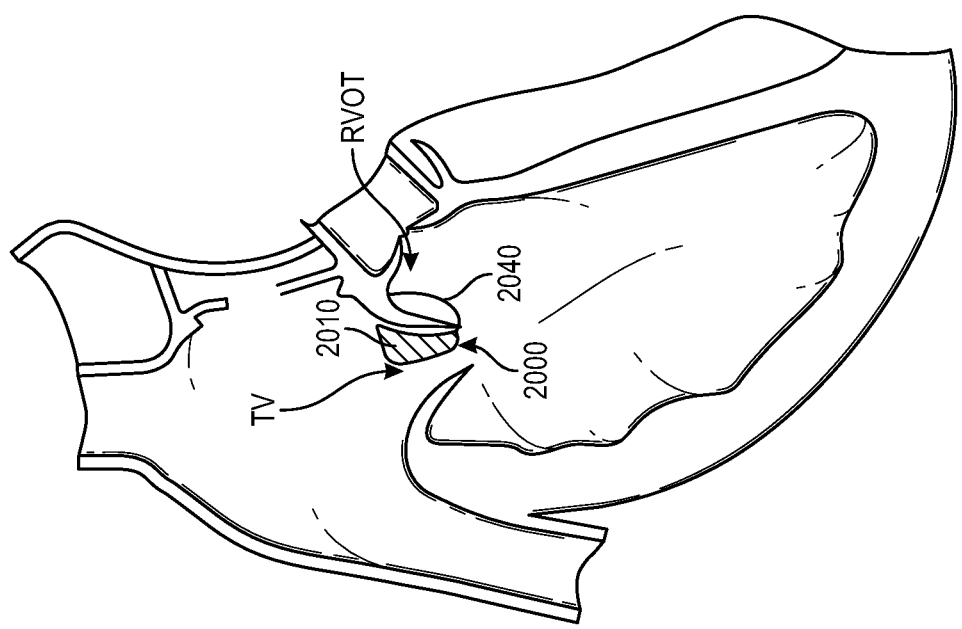
FIG. 20A is a side cross-sectional view of a valve repair device implanted at the tricuspid valve in accordance with embodiments of the present technology.

FIG. 20A is a side cross-sectional view of a valve repair device 2000 implanted at the tricuspid valve TV in accordance with embodiments of the present technology. FIGS. 20B and 20C are transverse cross-sectional views of the valve repair device 2000 of FIG. 20A during diastole and systole, respectively, in accordance with embodiments of the present technology. Referring to FIGS. 20A-20C together, the valve repair device 2000 includes a coaptation member 2010 and a pair of stabilization members 2040 (which can also be referred to as "anchoring mechanisms," "extensions," and the like) extending from the coaptation member 2010 into the right ventricular outflow tract RVOT. The stabilization members 2040 can be anchored (e.g., fixed, attached) within the right ventricular outflow tract RVOT, or can be unanchored and merely press against anatomy thereof to secure the coaptation member 2010 in position relative to the native leaflets of the tricuspid valve TV. In some embodiments, the coaptation member 2010 and the operation of the valve repair device 2000 can be generally similar or identical to that of the tricuspid valve repair devices 200 and/or 1400 described in detail above with reference to FIGS. 2A-2D and 14A-14E. For example, the stabilization members 2040 can secure the coaptation member 2010 to one of the native leaflets (e.g., the leaflet L1) such that the coaptation member 2010 replaces all or part of the native leaflet while providing a coaptation surface for one or more of the other native leaflets (e.g., the leaflets L2 and L3).

Figure 23:
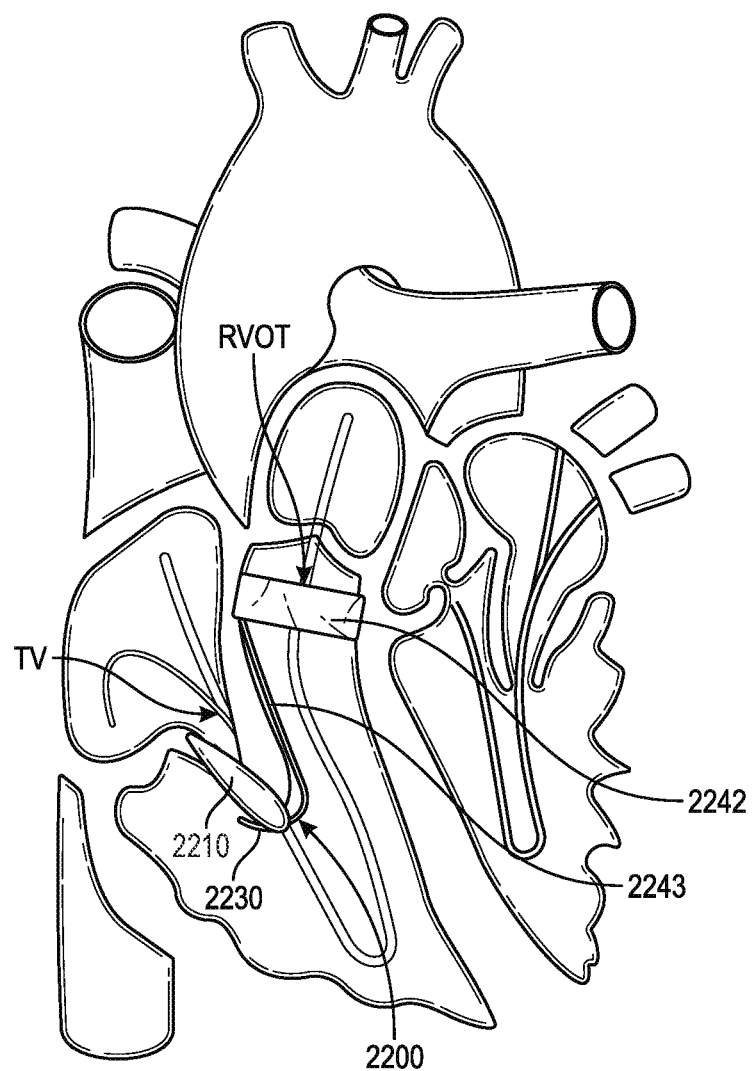
FIG. 23 is a side cross-sectional view of the valve repair device of FIG. 22 implanted at the tricuspid valve and secured to the anterior and/or posterior leaflets of the tricuspid valve in accordance with embodiments of the present technology.
Figure 24B:
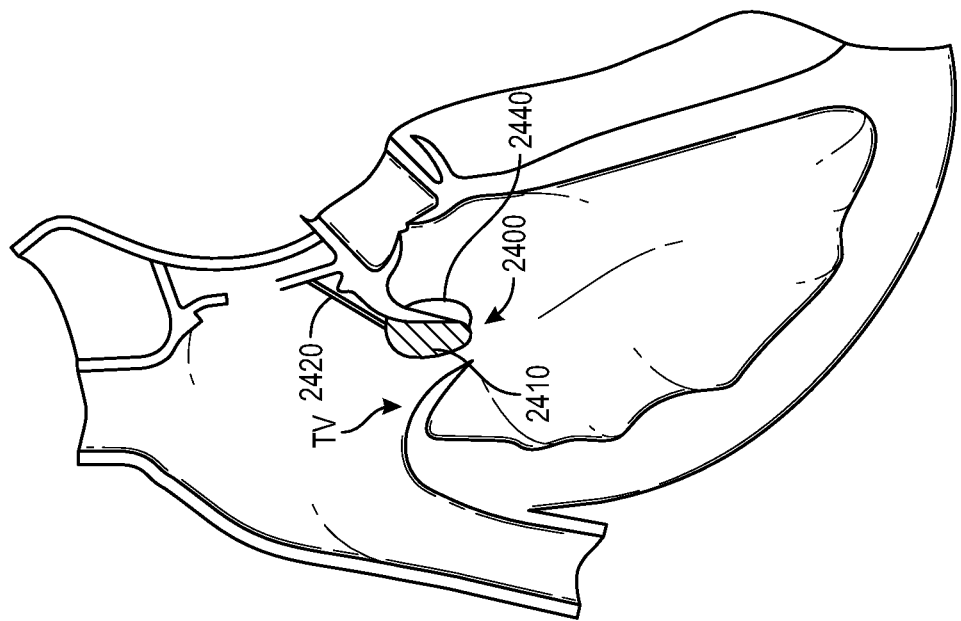
FIGS. 24A and 24B are side cross-sectional views of a valve repair device implanted at the tricuspid valve in a first position and a second position, respectively, in accordance with embodiments of the present technology.
Figure 24A:
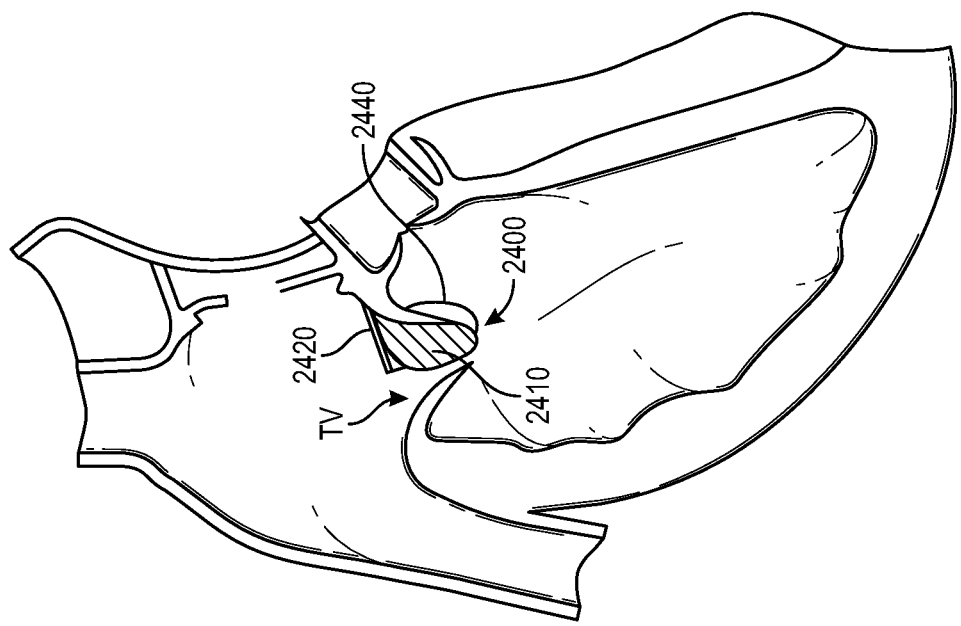

In some embodiments, the valve repair device 2000 can further include an atrial stabilization member. For example, FIG. 24A is a side cross-sectional view of the valve repair device 2000 of FIGS. 23A-23C further including an atrial stabilization member 2120 and implanted at the tricuspid valve TV in accordance with additional embodiments of the present technology. FIGS. 24B and 24C are transverse cross-sectional views of the valve repair 2000 device of FIG. 24A during diastole and systole, respectively, in accordance with embodiments of the present technology. Referring to FIGS. 24A-24C together, the atrial stabilization member 2120 is configured to anchor or brace against the septal wall above the tricuspid valve TV, as best seen in FIG. 24A, to help secure the position of the coaptation member 2010 between the native leaflets together with the ventricular stabilization members 2040 that reside within the right ventricular outflow tract RVOT.

Figure 22:
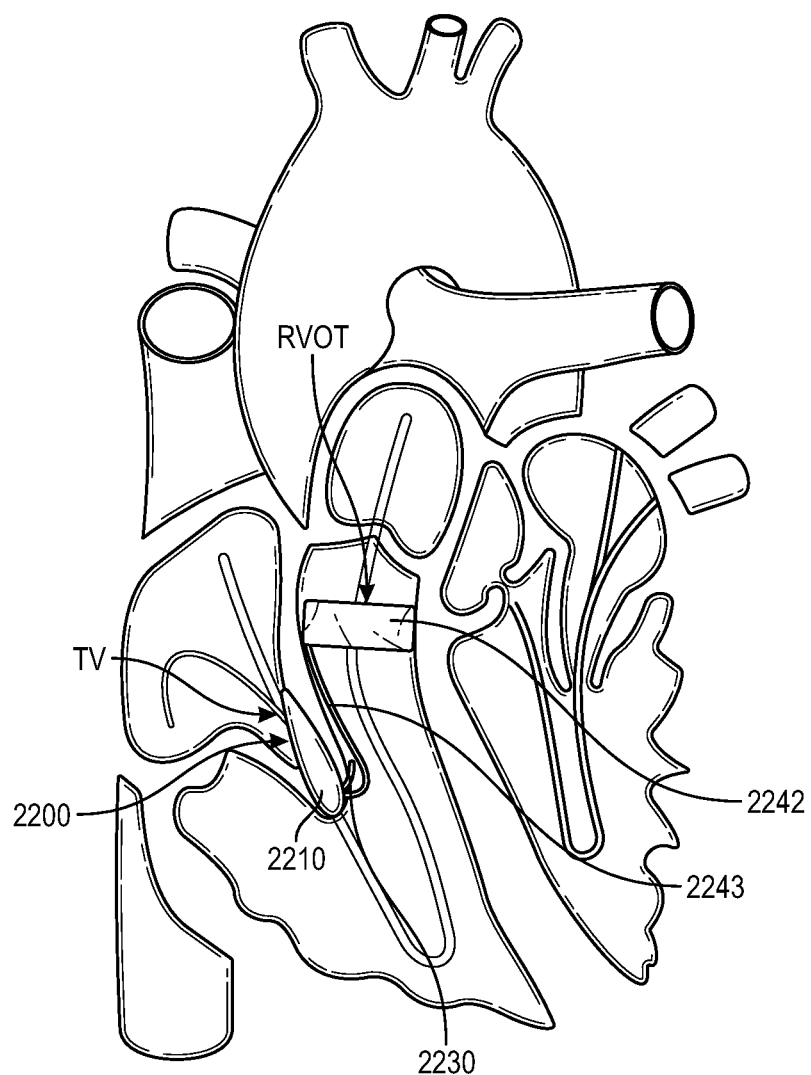
FIG. 22 is a side cross-sectional view of a valve repair device implanted at the tricuspid valve in accordance with embodiments of the present technology.

FIG. 22 is a side cross-sectional view of a valve repair device 2200 implanted at the tricuspid valve TV in accordance with embodiments of the present technology. In the illustrated embodiment, the valve repair device 2200 includes a coaptation member 2210 fixed to one or more of the native leaflets (e.g., the septal leaflet) of the tricuspid valve TV via a clip mechanism 2230. The valve repair device 2200 can further include an anchor 2242 secured in the right ventricular outflow tract RVOT, and a tether 2243 (also referred to as a "support element", "connector," and the like) extending between the coaptation member 2210 and the anchor 2242. In some embodiments, the anchor 2242 can include a laser-cut stent, braded stent, mesh and/or other element that imparts a radially outward force against the right ventricular outflow tract RVOT to secure (e.g., fix) the anchor 2242 in position. In some embodiments, the anchor 2242 can include a braided porous mesh (e.g., a filter) configured to permit blood flow into the pulmonary artery. In some embodiments, the anchor 2242 can include atraumatic frictional elements (not shown) on an outer surface thereof and configured to further fix the anchor 2242 in the right ventricular outflow tract RVOT. The tether 2243 can be a metallic wire, metallic suture, polymer suture, and/or another elongate element connected between the coaptation member 2210 and the anchor 2242.

In other embodiments, the coaptation member 2210 can be secured against one or more other native leaflets of the tricuspid valve TV. For example, FIG. 23 is a side cross-sectional view of the valve repair device 2200 of FIG. 22 implanted at the tricuspid valve TV and secured to the anterior and/or posterior leaflets in accordance with embodiments of the present technology. For example, the clip mechanism 2230 can be secured to a different one or more of the leaflets.

In some embodiments, a valve repair device in accordance with the present technology can further include an atrial stabilization member (also referred to as an "atrial fixation member") extending from the coaptation member into the right atrium and anchored to and/or secured against the septal wall or fossa. Such atrial stabilization members can include a braided mesh (e.g., an Amplatzer-style mesh or filter), a helical screw, and/or other support structures configured to anchor into the septal wall. The atrial stabilization member can inhibit or even prevent the coaptation from migrating into the right atrium, thereby inhibiting further prolapse of the native leaflets of the tricuspid valve TV. In some embodiments, the atrial stabilization member can include radiopaque or echogenic features that facilitate placement of the stabilization member (e.g., screws thereof) into the septal wall. In some embodiments, such an atrial stabilization member can be modularly added during a delivery procedure. For example, FIGS. 24A and 24B are side cross-sectional views of a valve repair device 2400 implanted at the tricuspid valve TV in a first position and a second position, respectively, in accordance with embodiments of the present technology. Referring to FIGS. 24A and 24B together, the valve repair device 2400 includes a coaptation member 2410, one or more stabilization members 2440, and an atrial stabilization member 2420. Referring to FIG. 24A, the valve repair device 2400 can first be deployed at the tricuspid valve TV with the atrial stabilization member 2420 in an undeployed state (e.g., not deployed into the septal wall or fossa). Referring next to FIG. 24B, the atrial stabilization member 2420 can be fixed to the septal wall or fossa to further secure the coaptation member 2410 at the tricuspid valve TV if, for example, testing determines that further stabilization is desired.

Figure 25B:
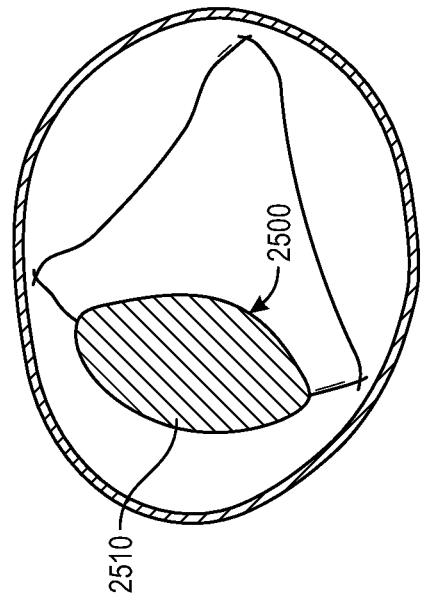
FIGS. 25B and 25C are transverse cross-sectional views of the valve repair device of FIG. 25A during diastole and systole, respectively, in accordance with embodiments of the present technology.
Figure 25C:
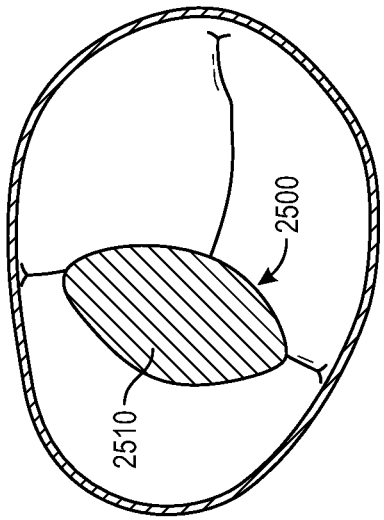
Figure 25A:
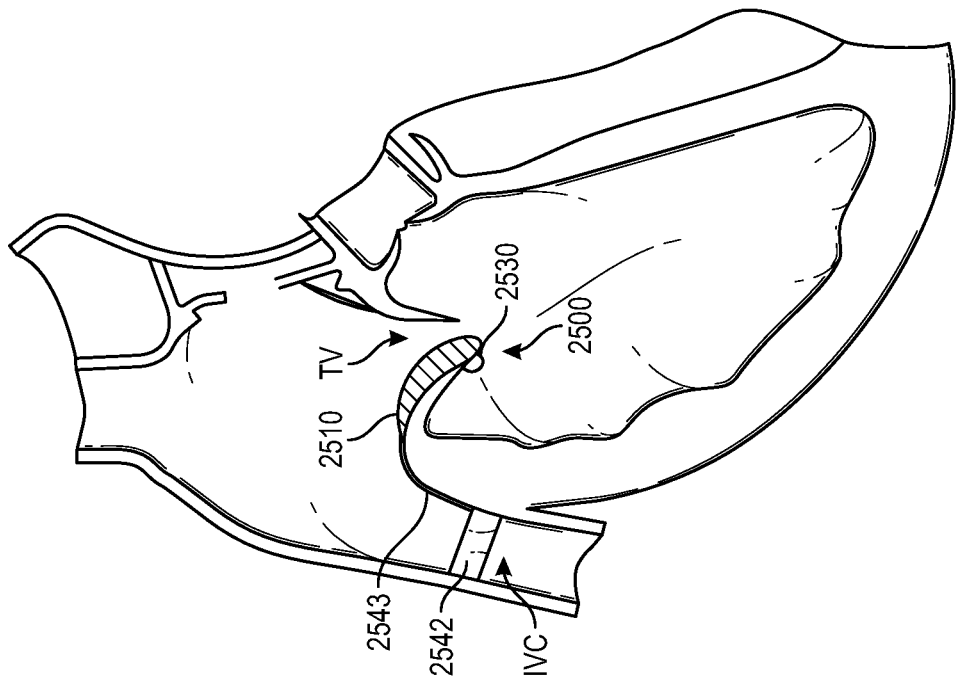
FIG. 25A is a side cross-sectional view of a valve repair device implanted at the tricuspid valve in accordance with embodiments of the present technology.

FIG. 25A is a side cross-sectional view of a valve repair device 2500 implanted at the tricuspid valve TV in accordance with embodiments of the present technology. FIGS. 25B and 25C are transverse cross-sectional views of the valve repair device 2500 of FIG. 25A during diastole and systole, respectively, in accordance with embodiments of the present technology. Referring to FIGS. 25A-25C together, the valve repair device 2500 includes a coaptation member 2510 fixed to one or more of the native leaflets of the tricuspid valve TV via a clip mechanism 2530. The valve repair device 2500 can further include an anchor 2542 secured in the inferior vena cava IVC, and a tether 2543 extending between the coaptation member 2510 and the anchor 2542. In some embodiments, the anchor 2542 can include a laser-cut stent, braded stent, mesh and/or other element that imparts a radially outward force against the inferior vena cava IVC to secure (e.g., fix) the anchor 2542 in position. The tether 2543 can be a metallic wire, metallic suture, polymer suture, and/or other elongate element connected to the coaptation member 2510 at an anchor connection point and configured to inhibit or even prevent atrial migration of the coaptation member 2510.

Figure 26:
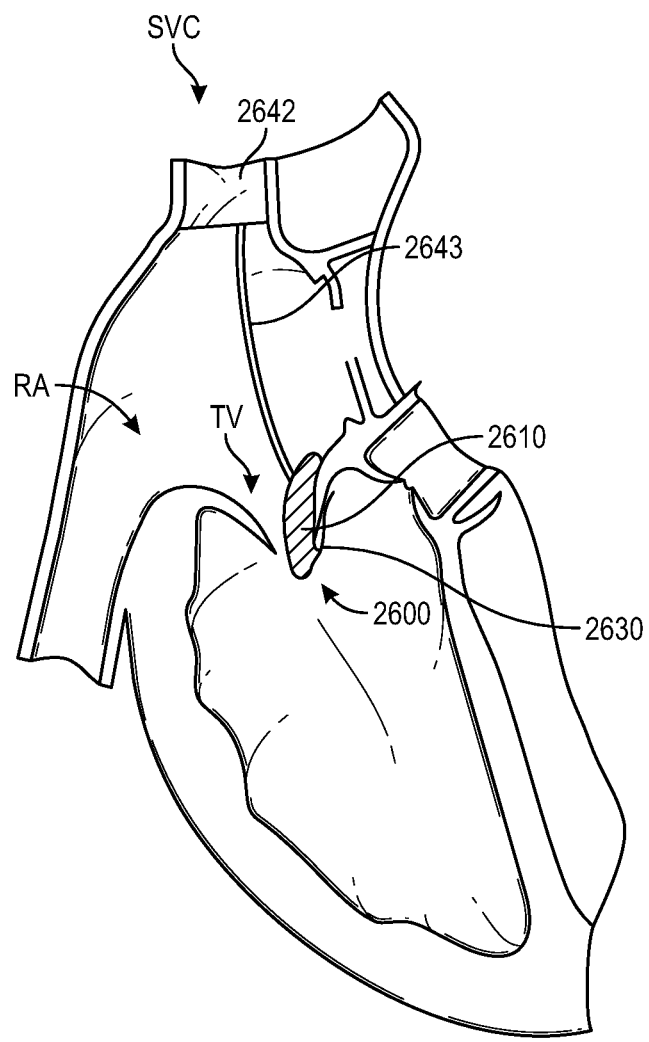
FIG. 26 is a side cross-sectional view of a valve repair device implanted at the tricuspid valve in accordance with embodiments of the present technology.

FIG. 26 is a side cross-sectional view of a valve repair device 2600 implanted at the tricuspid valve TV in accordance with embodiments of the present technology. In the illustrated embodiment, the valve repair device 2600 includes a coaptation member 2610 fixed to one or more of the native leaflets of the tricuspid valve TV via a clip mechanism 2630. The valve repair device 2600 can further include an anchor 2642 secured in the superior vena cava SVC, and a tether 2643 extending between the coaptation member 2610 and the anchor 2642. In some embodiments, the anchor 2642 can include a laser-cut stent, braded stent, mesh and/or other element that imparts a radially outward force against superior vena cava SVC to secure (e.g., fix) the anchor 2642 in position. The tether 2643 can be a metallic wire, metallic suture, polymer suture, and/or other stiff support element connected to the coaptation member 2610 and configured to inhibit or even prevent prolapse of the coaptation member 2610 into the right atrium RA.

Referring to FIGS. 20A-26 together, tricuspid valve repair devices in accordance with the present technology can include various combinations of the described and illustrated anchoring mechanisms, clip mechanisms, and/or support mechanisms to, for example, provide a specific support structure for a coaptation member based on the particular anatomy of a patient. For example, a clip mechanism can provide primary fixation for the coaptation member, while a ventricular anchor to the right ventricular outflow tract RVOT can be added modularly in flail conditions to inhibit or even prevent excessive atrial movement of the coaptation member from leaflet flail. Likewise, an atrial-side anchor to the superior vena cava SVC and/or the inferior vena cava IVC can be added to inhibit or even prevent atrial migration of the coaptation member.

Figure 27B:
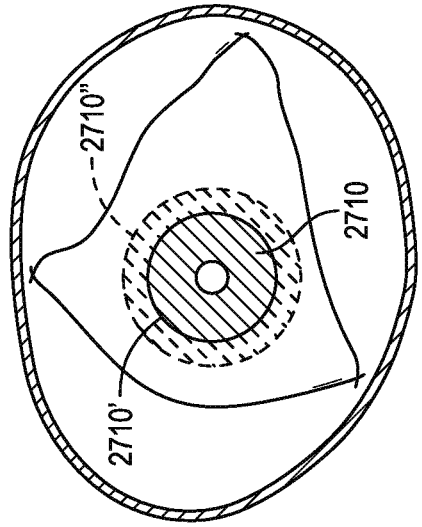
FIGS. 27B and 27C are transverse cross-sectional views of the valve repair device of FIG. 27A during diastole and systole, respectively, in accordance with embodiments of the present technology.
Figure 27C:
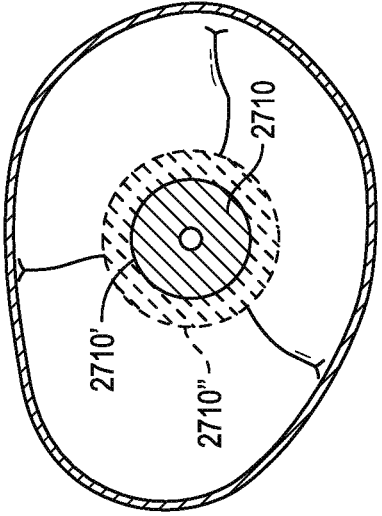
Figure 27A:
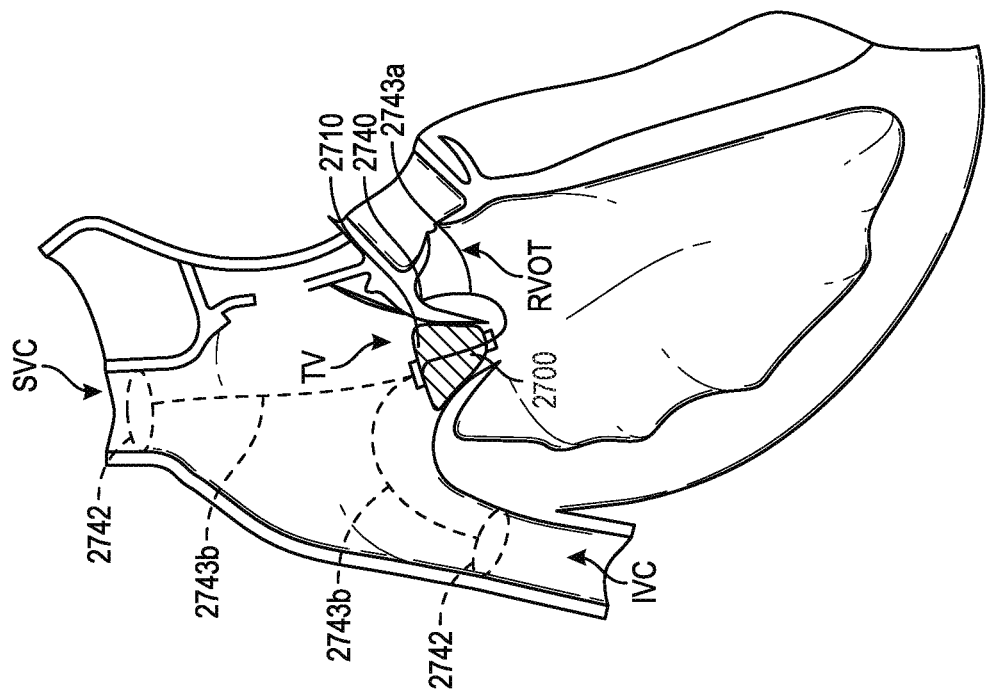
FIG. 27A is a side cross-sectional view of a valve repair device implanted at the tricuspid valve in accordance with embodiments of the present technology.

More specifically, for example, FIG. 27A is a side cross-sectional view of a valve repair device 2700 implanted at the tricuspid valve TV in accordance with embodiments of the present technology. FIGS. 27B and 27C are transverse cross-sectional views of the valve repair device 2700 of FIG. 27A during diastole and systole, respectively, in accordance with embodiments of the present technology. Referring to FIGS. 27A-27C together, the valve repair device 2700 includes a coaptation member 2710 secured at the tricuspid valve TV between the native leaflets via a first tether 2743*a* extending to an anchor 2740 in the right ventricular outflow tract RVOT—without a clip mechanism fixing the coaptation member 2710 to any of the native leaflets. The valve repair device 2700 can optionally include anchors 2742 in the inferior vena cava IVC and/or the superior vena cava SVC and connected to the coaptation member 2710 via second tethers 2743*b*. As shown in FIGS. 27B and 27C, in some embodiments the coaptation member 2710 can be adjustable (e.g., expandable) between a first (e.g., radially-compressed) position 2710' and a second (e.g., radially-expanded) position 2710".

V. ADDITIONAL EXAMPLES

The following examples are illustrative of several embodiments of the present technology:

1. A tricuspid valve repair device, comprising:
   a coaptation member configured to be positioned at least partially between native leaflets of a tricuspid valve;
   a clip mechanism coupled to the coaptation mechanism, wherein the clip mechanism is configured to engage a ventricular side of one of the native leaflets to secure the one of the native leaflets between the clip mechanism and the coaptation member, and wherein the coaptation member includes a surface configured to coapt with at least another one of the native leaflets; and
   a stabilization member extending from the coaptation member and configured to be positioned at least partially within a right atrium above the tricuspid valve, wherein the stabilization member is configured to contact a wall within the right atrium to stabilize a position of the coaptation member relative to the tricuspid valve.

2. The tricuspid valve repair device of example 1 wherein the one of the native leaflets is a native septal leaflet of the tricuspid valve.

3. The tricuspid valve repair device of example 1 or example 2 wherein the wall within the right atrium is a septal wall between the right atrium and a left atrium.

4. The tricuspid valve repair device of any one of examples 1-3 wherein the one of the native leaflets is a native septal leaflet of the tricuspid valve, and wherein the wall within the right atrium is a septal wall between the right atrium and a left atrium.

5. The tricuspid valve repair device of any one of examples 1-4 wherein the stabilization member includes a frame and a covering over the frame.

6. The tricuspid valve repair device of example 5 wherein the frame is formed from a metal material, and wherein the covering is formed from at least one of a fabric material, an extruded polymeric material, and a graft material.

7. The tricuspid valve repair device of example 5 or example 6 wherein the frame has an M-like shape.

8. The tricuspid valve repair device of example 5 or example 6 wherein the frame includes two or more wireform loops extending from the coaptation member.

9. The tricuspid valve repair device of any one of examples 1-8 wherein the coaptation member extends radially inward from the stabilization member toward a flow axis of the tricuspid valve, and wherein the stabilization member extends from the coaptation member at an angle relative to the flow axis.

10. The tricuspid valve repair device of any one of examples 1-9 wherein the clip mechanism is one of a plurality of clip mechanisms, wherein each of the clip mechanisms is configured to engage the ventricular side of the one of the native leaflets to secure the one of the native leaflets between the clip mechanism and the coaptation member.

11. The tricuspid valve repair device of any one of examples 1-10 wherein the stabilization member includes an upper portion with a chevron-like shape.

12. The tricuspid valve repair device of example 11 wherein the coaptation member includes an upper portion with a chevron-like shape.

13. The tricuspid valve repair device of any one of examples 1-12, further comprising a puncture member coupled to the stabilization member and configured to puncture the wall within the right atrium to further stabilize the position of the coaptation member relative to the tricuspid valve.

14. A tricuspid valve repair device, comprising:
a coaptation member configured to be positioned at least partially between a native septal leaflet, a native posterior leaflet, and a native anterior leaflet of a tricuspid valve, wherein the coaptation member includes a first surface and a second surface;
multiple clip mechanisms coupled to the coaptation mechanism, wherein each of the clip mechanisms is configured to engage a ventricular side of the native septal leaflet to secure the native septal leaflet between the clip mechanism and the first surface of the coaptation member, and wherein the at second surface of the coaptation member is configured to coapt with at least one of the native anterior leaflet and the native posterior leaflet; and
a stabilization member extending from the coaptation member and configured to be positioned at least partially within a right atrium above the tricuspid valve, wherein the stabilization member is configured to contact a septal between the right atrium and a left atrium to (a) stabilize a position of the coaptation member relative to the tricuspid valve and (b) provide a platform for tissue ingrowth and long-term fixation.

15. The tricuspid valve repair device of example 14 wherein the tricuspid valve includes a flow axis, and wherein the stabilization member extends away from the coaptation member toward the septal wall at an angle relative to the flow axis.

16. The tricuspid valve repair device of example 14 or example 15 wherein the stabilization member includes a wireform extending from the coaptation member and a covering over the wireform.

17. A method of repairing a tricuspid valve, the method comprising:
deploying a coaptation member of a tricuspid valve repair device at least partially between native leaflets of a tricuspid valve;
engaging a ventricular side of one of the native leaflets with a clip mechanism of the tricuspid valve repair device to secure the one of the native leaflets between the clip mechanism and a first surface of the coaptation member;
positioning the coaptation member such that a second surface of the coaptation member is configured to coapt with at least another one of the native leaflets; and
contacting a stabilization member of the tricuspid valve repair device with a wall within a right atrium above the tricuspid valve to stabilize a position of the coaptation member relative to the tricuspid valve.

18. The method of example 17 wherein the one of the native leaflets is a native septal leaflet of the tricuspid valve.

19. The method of example 17 or example 18 wherein the wall within the right atrium is a septal wall between the right atrium and a left atrium.

20. The method of any one of examples 17-19 wherein the one of the native leaflets is a native septal leaflet of the tricuspid valve, and wherein the wall within the right atrium is a septal wall between the right atrium and a left atrium.

VI. CONCLUSION

The above detailed description of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments can perform steps in a different order. The various embodiments described herein can also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms can also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications can be made without deviating from the technology. Further, while advantages associated with some embodiments of the technology have been described in the context of those embodiments, other embodiments can also exhibit such advantages, and not all embodiments need necessarily exhibit such advantages to fall within the scope of the technology. Accordingly, the disclosure and associated technology can encompass other embodiments not expressly shown or described herein.

so on.

We claim:

1. A tricuspid valve repair device, comprising:
a coaptation member configured to be positioned at least partially between a first native leaflet and a second native leaflet of a tricuspid valve;

a plurality of clip mechanisms coupled to the coaptation member, wherein each of the clip mechanisms is configured to clamp against a ventricular side of the first native leaflet to secure the first native leaflet between the clip mechanism and the coaptation member, and wherein the coaptation member includes a surface configured to coapt with at least the second native leaflet; and a stabilization member extending from the coaptation member and configured to be positioned at least partially within a right atrium above the tricuspid valve, wherein the stabilization member is shaped to extend along and press against an atrial side of the first native leaflet and a wall within the right atrium above the first native leaflet to stabilize a position of the coaptation member relative to the tricuspid valve, and wherein the stabilization member is biased outwardly from the coaptation member to push a portion of the first native leaflet back from an opening of the tricuspid valve.

2. The tricuspid valve repair device of claim 1 wherein the first native leaflet is a native septal leaflet of the tricuspid valve.

3. The tricuspid valve repair device of claim 1 wherein the wall within the right atrium is a septal wall between the right atrium and a left atrium.

4. The tricuspid valve repair device of claim 1 wherein the first native leaflet is a native septal leaflet of the tricuspid valve, and wherein the wall within the right atrium is a septal wall between the right atrium and a left atrium.

5. The tricuspid valve repair device of claim 1 wherein the stabilization member includes a frame and a covering over the frame.

6. The tricuspid valve repair device of claim 5 wherein the frame is formed from a metal material, and wherein the covering is formed from at least one of a fabric material, an extruded polymeric material, and a graft material.

7. The tricuspid valve repair device of claim 5 wherein the frame has an M-like shape.

8. The tricuspid valve repair device of claim 5 wherein the frame includes two or more wireform loops extending from the coaptation member.

9. The tricuspid valve repair device of claim 1 wherein the coaptation member extends radially inward from the stabilization member toward a flow axis of the tricuspid valve, and wherein the stabilization member extends from the coaptation member at an angle relative to the flow axis.

10. The tricuspid valve repair device of claim 1 wherein the stabilization member includes an upper portion with a chevron-like shape.

11. The tricuspid valve repair device of claim 10 wherein the coaptation member includes an upper portion with a chevron-like shape.

12. The tricuspid valve repair device of claim 1, further comprising a puncture member coupled to the stabilization member and configured to puncture the wall within the right atrium to further stabilize the position of the coaptation member relative to the tricuspid valve.

13. The tricuspid valve repair device of claim 1 wherein the stabilization member is shaped to extend along and press against the atrial side of the first native leaflet and the wall within the right atrium above the first native leaflet to substantially maintain the coaptation member in a substantially stationary position relative to the tricuspid valve during cardiac cycles.

14. The tricuspid valve repair device of claim 1 wherein the stabilization member comprises a frame made of stent material that provides lateral stiffness and torsional and front-to-back stability to reduce loads transferred to and/or from the coaptation member.

15. The tricuspid valve repair device of claim 1 wherein the stabilization member comprises a frame shaped to track a shape of and brace against the wall within the right atrium above a native valve annulus.

16. The tricuspid valve repair device of claim 1 wherein the stabilization member comprises a frame with an elongate shape extending away from the coaptation member and configured to be positioned above a native valve annulus.

17. The tricuspid valve repair device of claim 1 wherein the stabilization member comprises a frame configured to stabilize the position of the coaptation member relative to the tricuspid valve without penetrating cardiac tissue.

18. The tricuspid valve repair device of claim 1 wherein the stabilization member is angled from the coaptation member by an angle between 10-75 degrees.

19. A tricuspid valve repair device, comprising:
a coaptation member configured to be positioned at least partially between a native septal leaflet, a native posterior leaflet, and a native anterior leaflet of a tricuspid valve, wherein the coaptation member includes a first surface and a second surface;
multiple clip mechanisms coupled to the coaptation member, wherein each of the clip mechanisms is configured to move from an open state to a closed state, wherein—
in the open state, an arm member of the clip mechanism extends away from the coaptation member to allow a free end portion of the arm member to extend behind the native septal leaflet,
in the closed state, the arm member presses against a ventricular side of the native septal leaflet and the first surface of the coaptation member to secure the native septal leaflet between the clip mechanism and the first surface of the coaptation member, and
the second surface of the coaptation member is configured to coapt with at least one of the native anterior leaflet and the native posterior leaflet; and
a stabilization member extending from the coaptation member and configured to be positioned at least partially within a right atrium above the tricuspid valve, wherein the stabilization member is shaped to extend along and press against an atrial side of the native septal leaflet and a septal wall between the right atrium and a left atrium to (a) stabilize a position of the coaptation member relative to the tricuspid valve and (b) provide a platform for tissue ingrowth and long-term fixation, and wherein the stabilization member is biased outwardly from the coaptation member to push a portion of the native septal leaflet back from an opening of the tricuspid valve.

20. The tricuspid valve repair device of claim 19 wherein the tricuspid valve includes a flow axis, and wherein the stabilization member extends away from the coaptation member toward the septal wall at an angle relative to the flow axis.

21. The tricuspid valve repair device of claim 19 wherein the stabilization member includes a wireform extending from the coaptation member and a covering over the wireform.

22. The tricuspid valve repair device of claim 19 wherein the stabilization member is shaped to extend along and press against the atrial side of the native septal leaflet and the septal wall between the right atrium and the left atrium to substantially maintain the coaptation member in a substantially stationary position relative to the tricuspid valve during cardiac cycles.

23. A method of repairing a tricuspid valve, the method comprising:
   deploying a coaptation member of a tricuspid valve repair device at least partially between a first native leaflet and a second native leaflet of a tricuspid valve;
   grasping a first portion of a ventricular side of the first native leaflet with a first clip mechanism of the tricuspid valve repair device; and
   grasping a second portion of the ventricular side of the first native leaflet with a second clip mechanism of the tricuspid valve repair device to secure the first native leaflet between the first and second clip mechanisms and a first surface of the coaptation member;
   positioning the coaptation member such that a second surface of the coaptation member is configured to coapt with at least the second native leaflet; and
   contacting a stabilization member of the tricuspid valve repair device with an atrial side of the first native leaflet and a wall within a right atrium above the first native leaflet to stabilize a position of the coaptation member relative to the tricuspid valve, wherein the stabilization member is biased outwardly from the coaptation member to push a portion of the first native leaflet back from an opening of the tricuspid valve.

24. The method of claim 23 wherein the one of the native leaflets is a native septal leaflet of the tricuspid valve.

25. The method of claim 23 wherein the wall within the right atrium is a septal wall between the right atrium and a left atrium.

26. The method of claim 23 wherein the one of the native leaflets is a native septal leaflet of the tricuspid valve, and wherein the wall within the right atrium is a septal wall between the right atrium and a left atrium.

27. The method of claim 23 wherein contacting the stabilization member of the tricuspid valve repair device with the atrial side of the first native leaflet and the wall within the right atrium above the first native leaflet further comprises contacting the stabilization member with the atrial side of the first native leaflet and the wall within the right atrium above the first native leaflet to substantially maintain the coaptation member in a substantially stationary position relative to the tricuspid valve during cardiac cycles.

* * * * *

UNITED STATES PATENT AND TRADEMARK OFFICE
CERTIFICATE OF CORRECTION

| | | |
|---|---|---|
| PATENT NO. | : 12,414,855 B2 | Page 1 of 1 |
| APPLICATION NO. | : 17/456153 | |
| DATED | : September 16, 2025 | |
| INVENTOR(S) | : Katherine Miyashiro et al. | |

It is certified that error appears in the above-identified patent and that said Letters Patent is hereby corrected as shown below:

In the Specification

In Column 18, Line 1, "FIG. 24A" should read --FIG. 21A--

In Column 18, Line 2, "FIG. 23A-23C" should read --FIG. 20A-20C--

In Column 18, Line 5, "FIGS. 24B and 24C" should read --FIGS. 21B and 21C--

In Column 18, Line 7, "24A" should read --21A--

In Column 18, Line 9, "FIGS. 24A-24C" should read --FIGS. 21A-21C--

In Column 18, Line 11, "FIG. 24A" should read --FIG. 21A--

Signed and Sealed this
Twenty-fifth Day of November, 2025

John A. Squires
*Director of the United States Patent and Trademark Office*